US011113856B2

(12) United States Patent
Shinohara et al.

(10) Patent No.: US 11,113,856 B2
(45) Date of Patent: Sep. 7, 2021

(54) INFORMATION DISPLAYING SYSTEM AND INFORMATION DISPLAYING DEVICE

(71) Applicants: Michinari Shinohara, Kanagawa (JP); Yutaka Yagiura, Kanagawa (JP); Daisuke Sakai, Tokyo (JP)

(72) Inventors: Michinari Shinohara, Kanagawa (JP); Yutaka Yagiura, Kanagawa (JP); Daisuke Sakai, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 16/192,990

(22) Filed: Nov. 16, 2018

(65) Prior Publication Data

US 2019/0087996 A1     Mar. 21, 2019

Related U.S. Application Data

(63) Continuation of application No. 15/987,260, filed on May 23, 2018, now Pat. No. 11,037,349, which is a
(Continued)

(30) Foreign Application Priority Data

Nov. 30, 2016  (JP) .............................. JP2016-233405
May 17, 2017   (JP) .............................. JP2017-098525

(51) Int. Cl.
  *G06T 11/60*    (2006.01)
  *G09G 5/14*     (2006.01)
  (Continued)

(52) U.S. Cl.
  CPC .............. *G06T 11/60* (2013.01); *A61B 5/245* (2021.01); *A61B 5/291* (2021.01); *A61B 5/369* (2021.01);
  (Continued)

(58) Field of Classification Search
CPC combination set(s) only.
See application file for complete search history.

(56) References Cited

U.S. PATENT DOCUMENTS 5,262,944 A  *  11/1993  Weisner ................. A61B 5/044
                                                600/300
5,880,588 A     3/1999  Kado
                (Continued)

FOREIGN PATENT DOCUMENTS

JP      H09-016654      1/1997
JP      H11-104092      4/1999
                (Continued)

OTHER PUBLICATIONS

International Search Report dated Jan. 5, 2018 in PCT/JP2017/036592 filed on Oct. 10, 2017.
(Continued)

*Primary Examiner* — Motilewa Good Johnson
(74) *Attorney, Agent, or Firm* — IPUSA, PLLC

(57) ABSTRACT

An information displaying system is configured to display a time axis region and a signal display region on a display device. The time axis region is configured to display a time axis of a biosignal along a first direction and to display a first mark on the time axis, and signal display region is configured to display a plurality of waveforms of the biosignal side by side in a second direction which is different from the first direction. In response to receiving a designation information designating a time, the information displaying system displays, on the signal display region, the plurality of waveforms for a predetermined time range including the time designated by the designation information, and displays a line extending in the second direction at a location of the waveforms corresponding to the first mark.

11 Claims, 31 Drawing Sheets

Related U.S. Application Data continuation of application No. PCT/JP2017/036592, filed on Oct. 10, 2017.

(51) Int. Cl.

| | | |
|---|---|---|
| *A61B 5/00* | (2006.01) | |
| *G16H 30/40* | (2018.01) | |
| *G16H 40/63* | (2018.01) | |
| *G01R 33/02* | (2006.01) | |
| *G16H 40/60* | (2018.01) | |
| *G06F 3/147* | (2006.01) | |
| *G16H 30/20* | (2018.01) | |
| *G06T 11/20* | (2006.01) | |
| *G06F 40/169* | (2020.01) | |
| *A61B 5/245* | (2021.01) | |
| *A61B 5/291* | (2021.01) | |
| *A61B 5/369* | (2021.01) | |
| *G01V 3/08* | (2006.01) | |
| *G01R 33/56* | (2006.01) | |

(52) U.S. Cl.
CPC ............ *A61B 5/743* (2013.01); *A61B 5/7425* (2013.01); *G01R 33/02* (2013.01); *G06F 3/147* (2013.01); *G06F 40/169* (2020.01); *G06T 11/206* (2013.01); *G09G 5/14* (2013.01); *G16H 30/20* (2018.01); *G16H 30/40* (2018.01); *G16H 40/60* (2018.01); *G16H 40/63* (2018.01); *G01R 33/5608* (2013.01); *G01V 3/081* (2013.01); *G06T 2210/41* (2013.01); *G09G 2340/12* (2013.01); *G09G 2380/08* (2013.01)

(56) References Cited

U.S. PATENT DOCUMENTS

| | | | |
|---|---|---|---|
| 6,050,940 A | | 4/2000 | Braun et al. |
| 6,224,549 B1 | | 5/2001 | Drongelen |
| 6,356,256 B1 | * | 3/2002 | Leftwich ............... G06F 3/0481 345/1.1 |
| 6,473,639 B1 | * | 10/2002 | Fischell ............... A61B 5/0476 600/544 |
| 6,624,829 B1 | | 9/2003 | Beck et al. |
| 7,171,262 B2 | | 1/2007 | Yarita |
| 7,460,905 B2 | * | 12/2008 | Mase ..................... A61B 1/0005 600/544 |
| 7,895,527 B2 | | 2/2011 | Zaleski et al. |
| 8,140,919 B2 | * | 3/2012 | Glaser .................. G06F 11/327 714/57 |
| 8,223,151 B2 | | 7/2012 | Rule et al. |
| 8,325,188 B1 | | 12/2012 | Phillips et al. |
| 8,786,624 B2 | * | 7/2014 | Echauz ................ A61B 5/4094 345/589 |
| 9,058,696 B2 | * | 6/2015 | Omiya .................. G09G 5/363 |
| 9,135,331 B2 | * | 9/2015 | Rosenthal ............ G06F 3/0482 |
| 9,232,922 B2 | * | 1/2016 | Nierenberg ........ A61B 5/04017 |
| 9,811,928 B2 | * | 11/2017 | Park ...................... G01R 33/283 |
| 9,824,470 B2 | | 11/2017 | Kuo |
| 9,852,529 B2 | | 12/2017 | Kanada |
| 10,168,889 B2 | | 1/2019 | Freidhof |
| 10,631,825 B2 | * | 4/2020 | Lee ....................... G06F 3/0488 |
| 2004/0051721 A1 | | 3/2004 | Ramseth |
| 2004/0260192 A1 | * | 12/2004 | Yamamoto ............ A61B 5/044 600/523 |
| 2007/0203816 A1 | * | 8/2007 | Costache ............... G06Q 40/00 705/35 |
| 2007/0271067 A1 | * | 11/2007 | Cohn ............... G01R 31/31708 702/183 |
| 2008/0252642 A1 | | 10/2008 | Hansen et al. |
| 2009/0005703 A1 | * | 1/2009 | Fasciano ................ A61B 5/031 600/561 |
| 2009/0054800 A1 | | 2/2009 | Martinerie et al. |
| 2011/0201911 A1 | * | 8/2011 | Johnson ............. A61B 5/14532 600/365 |
| 2011/0271173 A1 | | 11/2011 | Aït-Mokhtar et al. |
| 2011/0282225 A1 | * | 11/2011 | Anderson ............ A61B 5/283 600/510 |
| 2012/0150446 A1 | | 6/2012 | Chang et al. |
| 2012/0278099 A1 | * | 11/2012 | Kelly ..................... G16H 10/60 705/3 |
| 2012/0278763 A1 | * | 11/2012 | Dees ................... G01R 13/0236 715/835 |
| 2013/0187923 A1 | * | 7/2013 | Yoshimoto ............ G06T 11/206 345/440 |
| 2013/0187948 A1 | * | 7/2013 | Yoshimoto ............ G06F 3/04883 345/629 |
| 2013/0245463 A1 | | 9/2013 | Stuebe et al. |
| 2014/0275819 A1 | * | 9/2014 | Kassem ................ A61B 5/743 600/301 |
| 2014/0347388 A1 | | 11/2014 | Friedman et al. |
| 2014/0364753 A1 | | 12/2014 | Zhang |
| 2015/0109307 A1 | | 4/2015 | Baartz |
| 2015/0227702 A1 | * | 8/2015 | Krishna ............... A61B 5/4094 705/2 |
| 2015/0248534 A1 | * | 9/2015 | Krzywicki .......... G06F 3/04847 715/771 |
| 2015/0282726 A1 | | 10/2015 | Grube et al. |
| 2015/0355790 A1 | * | 12/2015 | O'Mahony ........... G06F 3/0482 715/771 |
| 2016/0124635 A1 | | 5/2016 | Covington et al. |
| 2016/0350488 A1 | * | 12/2016 | Stocker .................. G16H 10/60 |
| 2017/0277414 A1 | * | 9/2017 | Yamauchi ........... G06F 3/04845 |
| 2017/0357764 A1 | | 12/2017 | Fauss et al. |

FOREIGN PATENT DOCUMENTS

| | | |
|---|---|---|
| JP | 3368287 | 1/2003 |
| JP | 2005-095469 | 4/2005 |
| JP | 2006-026066 | 2/2006 |
| JP | 2010-233953 | 10/2010 |
| JP | 5057636 | 10/2012 |
| JP | 2013-059621 | 4/2013 |
| JP | 5473327 | 4/2014 |
| JP | 2015-082098 | 4/2015 |
| JP | 2018-004286 | 1/2018 |

OTHER PUBLICATIONS

Office Action issued in co-pending U.S. Appl. No. 15/987,260 dated Nov. 27, 2019.

Office Action dated Apr. 20, 2020 issued to related U.S. Appl. No. 15/987,260.

U.S. Non-Final Office Action for U.S. Appl. No. 15/987,260 dated Sep. 29, 2020.

* cited by examiner

FIG.7

Annotation List

☑ Show Markup on wave ——————— 180a

| No. | File | Time | Event | MEMO | Cluster |
|---|---|---|---|---|---|
| 2 ☐ | 001 | 00:09:30 | 🔥 | normal spike | B |
| 1 ☐ | 001 | 00:05:00 | 🔥 | strong spike | A |
| 0 ☐ | 000 | 00:00:00 |   | Dr.memo | A |

Exit Measurement

180

SIGNAL WAVEFORMS IN ONE MEASURED FILE

SIGNAL WAVEFORMS IN OTHER MEASURED FILE

312

SIGNAL WAVEFORMS IN ONE MEASURED FILE

SIGNAL WAVEFORMS IN OTHER MEASURED FILE

SIGNAL WAVEFORMS IN ONE MEASURED FILE

SIGNAL WAVEFORMS IN OTHER MEASURED FILE

INFORMATION DISPLAYING SYSTEM AND INFORMATION DISPLAYING DEVICE

CROSS-REFERENCE TO RELATED APPLICATION

The present application is a continuation of patent application Ser. No. 15/987,260 filed on May 23, 2018, which is a continuation application of International Application No. PCT/JP2017/036592 filed on Oct. 10, 2017, which claims priority to Japanese Patent Application No. 2017-098525 filed on May 17, 2017 and Japanese Patent Application No. 2016-233405 filed on Nov. 30, 2016. The contents of these applications are incorporated herein by reference in their entirety.

BACKGROUND OF THE INVENTION

1. Field of the Invention

The present disclosure relates to an information displaying technique, especially relates to the information displaying technique including function for adding an annotation to a plurality of signal waveforms.

2. Description of the Related Art

In a bio-information monitoring system, techniques to add a comment to a biosignal of a patient at an arbitrary timing during monitoring, to record the biosignal with the comment, and to display the data related to the recorded biosignal at an arbitrary timing are known (see Japanese Unexamined Patent Application Publication No. 2005-95469, for example). The system disclosed in the Japanese Unexamined Patent Application Publication No. 2005-95469 receives instruction from the user who is monitoring a waveform to designate the range of the waveform and saves the waveform with the comment. When displaying the waveform, the saved comment is displayed with the waveform on the screen. The comment is displayed at the blank space of the screen for displaying the waveform.

Further, according to another technique of displaying a waveform with a digital annotation on the chart portion for displaying physiological information, multiple types of physiological signals (e.g., fetal heart rate signal and intra-uterine pressure signal) may be plotted on the same time axis so that these signals are displayed in a synchronized manner (see Japanese Unexamined Patent Application Publication No. 2013-59621, for example).

SUMMARY OF THE INVENTION

An information displaying system according to an aspect of the present disclosure is configured to display a time axis region and a signal display region on a display device. The time axis region is configured to display a time axis of a biosignal along a first direction and to display a first mark on the time axis, and signal display region is configured to display a plurality of waveforms of the biosignal side by side in a second direction which is different from the first direction. In response to receiving a designation information designating a time, the information displaying system displays, on the signal display region, the plurality of waveforms for a predetermined time range including the time designated by the designation information, and displays a line extending in the second direction at a location of the waveforms corresponding to the first mark.

BRIEF DESCRIPTION OF THE DRAWINGS

FIG. 7 is a view of an updated annotation list;

DESCRIPTION OF THE EMBODIMENTS

The related arts for displaying digital annotation do not specifically teach how to input digital annotation to the multiple types of physiological signals and how to display the annotation. Also in the related art, each of the multiple types of physiological signals is illustrated as a single waveform.

In recent years, research for the nervous activity of the brain has been in progress, which has prompted the development of magnetoencephalograph and electroencephalograph. The magnetoencephalograph or the electroencephalograph collects faint signal waveforms from a large number of sensors to obtain one type of biosignal. In the related arts, when multiple types of biosignals are displayed in parallel, or when multiple signal waveforms obtained from a large number of sensors are displayed in parallel, it is difficult to recognize to which waveform the comment or the annotation is added.

The purpose of the present disclosure is to provide the information displaying technique to realize a display screen that facilitates recognizing the location (point or range (area)) of the signal waveform to be considered, when multiple signal waveforms are displayed on the same time axis.

Figure 1:
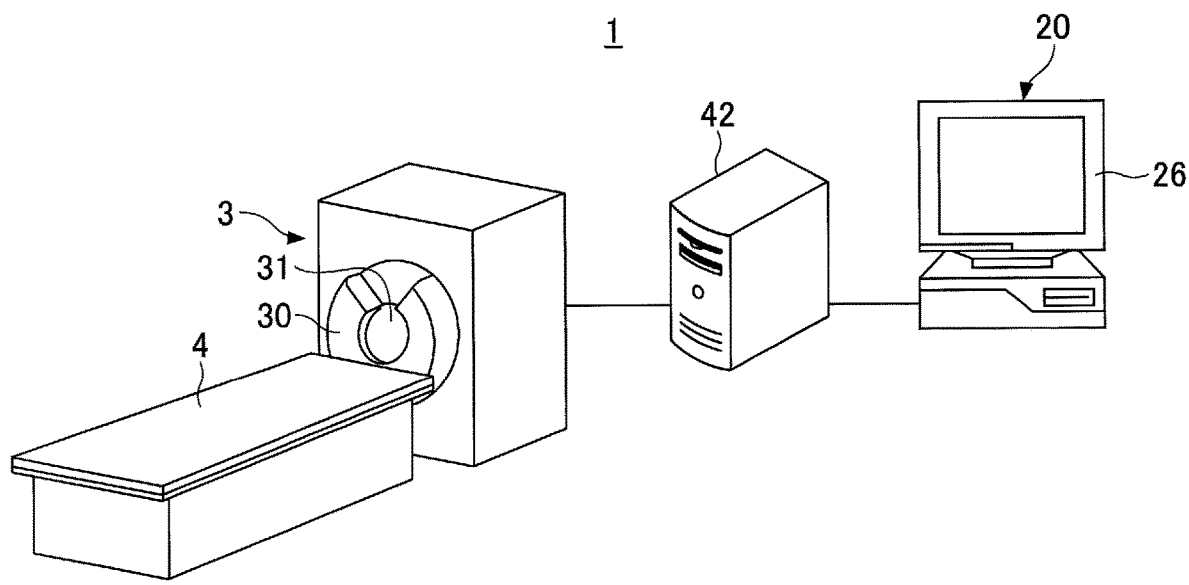
FIG. 1 is an external view of a biosignal measurement system where an information displaying technique according to the present disclosure is applied.

FIG. 1 is a schematic diagram of a biosignal measurement system 1 which is an application example of an information displaying technique according to the present embodiment. The biosignal measurement system 1 measures and displays multiple types of biosignals, for example, a magnetoencephalogram (MEG) signal and an electroencephalogram (EEG) signal. The biosignal measurement system 1 includes a measuring device 3, a data recording server 42, and an information displaying system 20. The information displaying system 20 includes a monitor display 26 to display signal information obtained by a measurement and analysis result. In FIG. 1, each of the data recording server 42 and the information displaying system 20 is illustrated as a distinct hardware, but at least a part of the components or the functions of the data recording server 42 may be incorporated in the information displaying system 20.

A person to be measured (hereinafter referred to as "subject") lies down on the measurement table 4 with electrodes (or sensors) on his/her head to measure the EEG signals, and inserts his/her head in a cavity 31 of a dewar 30 of the measuring device 3. The dewar 30 is a container for maintaining a cryogenic environment using liquid helium, and a large number of magnetic sensors for measuring the MEG signals reside inside the cavity 31 of the dewar 30. The measuring device 3 collects the EEG signals from the electrodes and collects the MEG signals from the magnetic sensors. The collected biosignals are stored in the data recording server 42. The information displaying system 20 reads the data recorded in the data recording server 42 to display and analyze the data. Generally, the dewar 30 including the magnetic sensors and the measurement table 4 are placed in the magnetic shield room, but in FIG. 1, the illustration of the magnetic shield room is omitted for convenience.

The information displaying system 20 displays the waveforms of the MEG signals obtained from the magnetic sensors and the waveforms of the EEG signals obtained from the electrodes in a synchronized manner so that each of the waveforms is displayed on the same time axis. An EEG signal represents an electrical activity of nerve cells (a flow of ion charge occurring at dendrite of a neuron during a synapse transmission) as the voltage between the electrodes. A MEG signal represents a faint variation of magnetic field occurring by the electrical activity in the brain. Brain magnetic field is detected by a superconducting quantum interferometer (SQUID) sensor of high sensitivity.

Figure 2:
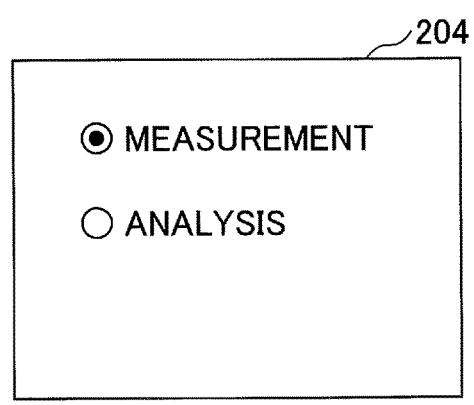
FIG. 2 is an example of starting screen of the information displaying system.

FIG. 2 illustrates an example of a starting screen 204 that is displayed on the monitor display 26. The selection boxes of "measurement" and "analysis" are displayed on the starting screen 204. When measuring at least one of the EEG signals and the MEG signals, data measurement is done by a different person from the one who analyzes the data. For instance, when the "measurement" box is selected by the laboratory technician (measurer), the data obtained by the measuring device 3 is stored (saved) in the data recording server 42 in succession. Additionally, the stored (saved) data is read by the information displaying system 20 and displayed on the monitor display 26. When the doctor selects "analysis" box after the measurement process is completed, the measured data recorded in the data recording server 42 is read out and analyzed. Detailed description of the process of measurement and the process of analysis will be explained below.

First Embodiment

<Operation of the Measurement Phase>

Figure 3:
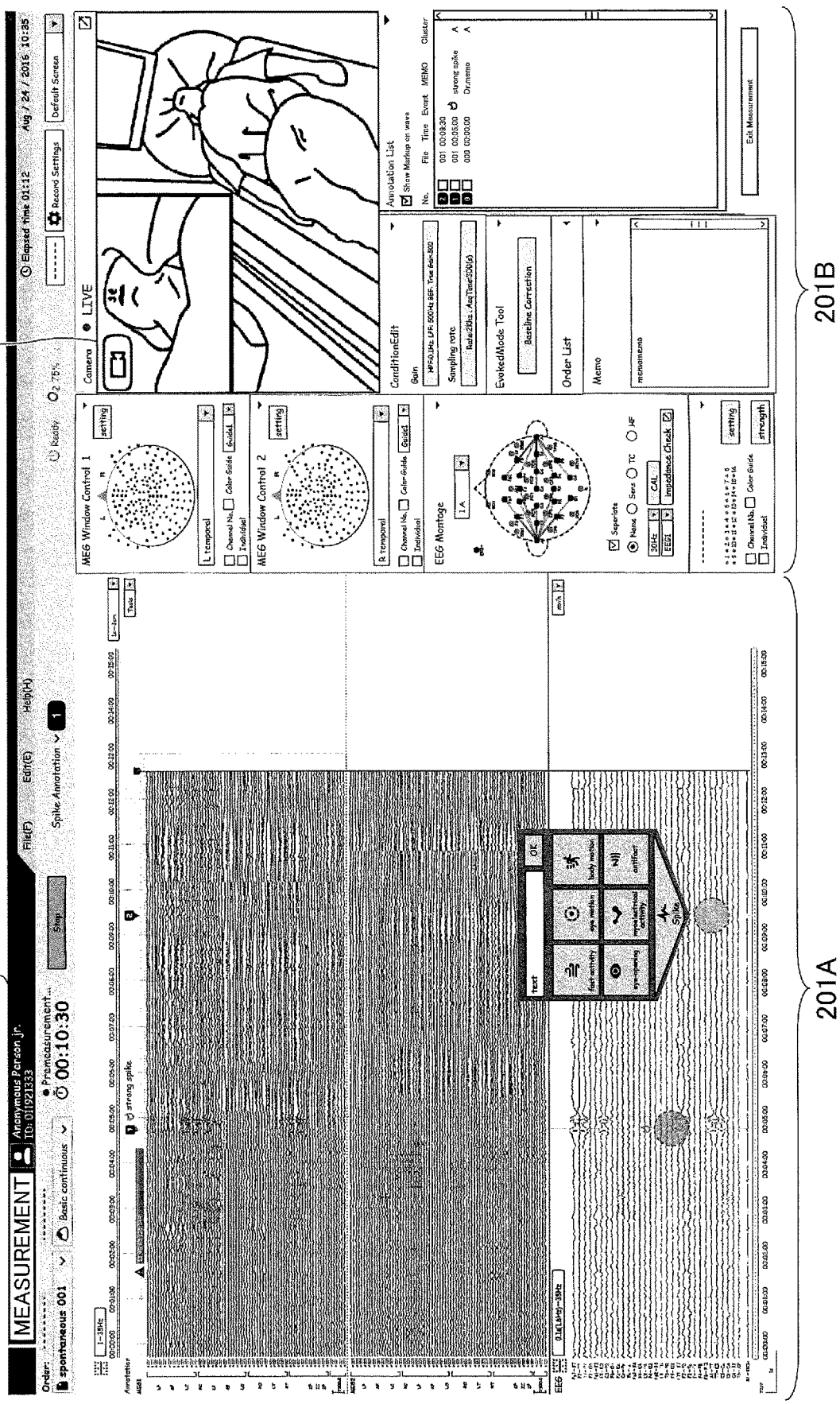
FIG. 3 is an example of a measurement screen.

FIG. 3 illustrates an example of a measurement screen. A tab 111 includes a label representing that this screen is for "measurement". The measurement screen includes a region 201A for displaying the measured signal waveforms, and a region 201B for displaying monitored information other than the signal waveforms. The region 201A for displaying the signal waveforms is placed on the left side of the screen seen from the measurer, and the region 201B for displaying the monitored information other than the signal waveforms is placed on the right side of the screen seen from the measurer. This placement improves the work efficiency of the measurer since the eye movement of the measurer that follows the movement of the waveforms detected and displayed in real-time (the waveforms move from left to right) is similar to the movement of the mouse cursor by the measurer that moves the mouse cursor from the region 201A in the left side of the screen to the region 201B in the right side of the screen.

The region 201B includes a monitor window 170 that enables to check the state of the subject during measurement. By displaying the live video image of the subject during measurement, the reliability of the check of the signal waveforms or the reliability of the determination will be improved, as will be explained later. In the example illustrated in FIG. 3, the entire measurement screen is displayed on the screen of the monitor display 26. Alternatively, the left side region 201A and the right side region 201B may be displayed separately on two or more different monitor displays.

Figure 4:
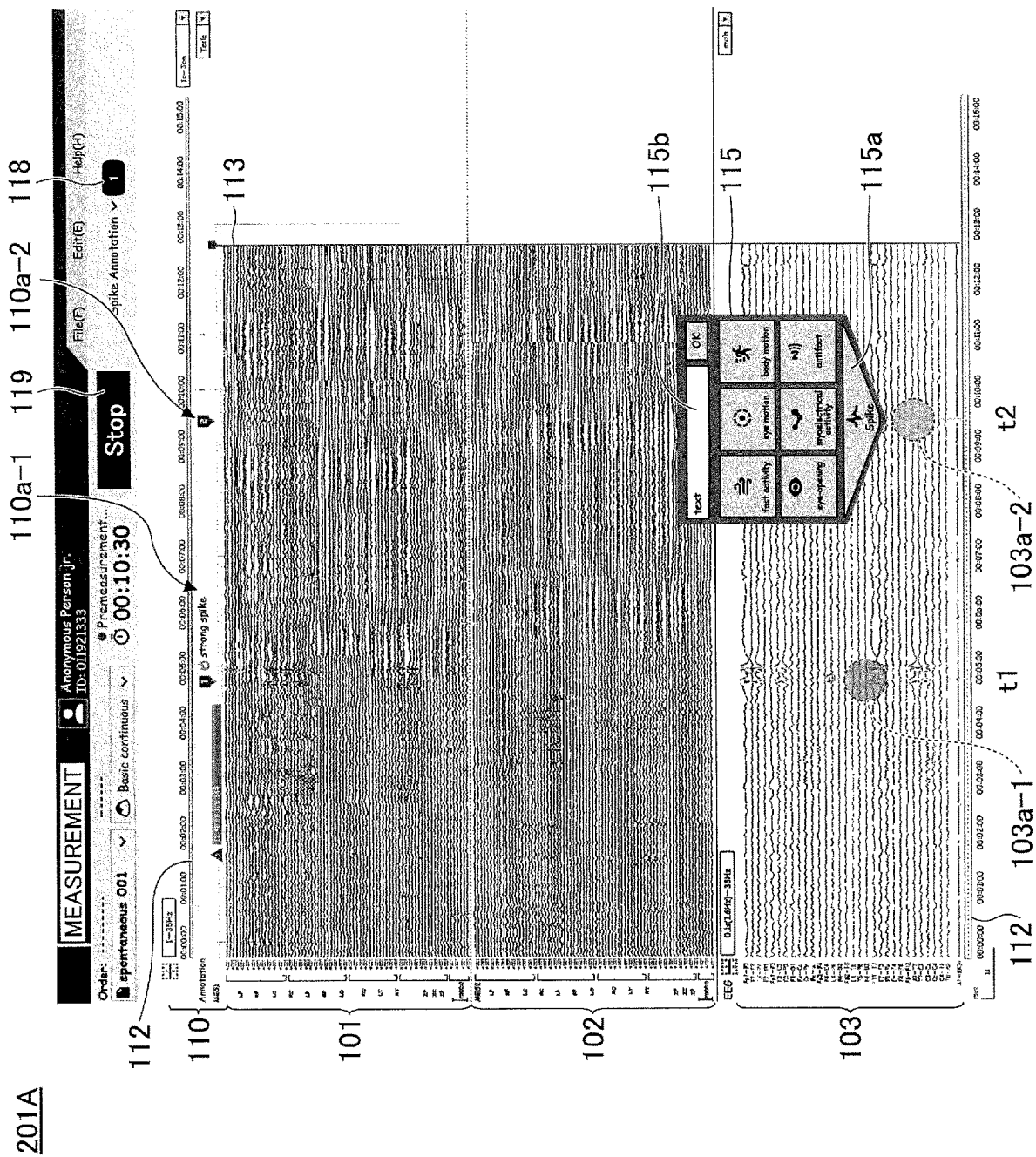
FIG. 4 is an enlarged view of the left region of the measurement screen in FIG. 3.

FIG. 4 is an enlarged view of the left side region 201A in FIG. 3. The region 201A includes a display section 110 which is a first display section for displaying information representing the time when a signal is detected (time information of signal detection) along a horizontal direction (first direction) of the screen, and display sections 101 through 103 which are a second display section for displaying multiple signal waveforms based on the signal detection in parallel so that the signal waveforms are arranged side by side in a vertical direction (second direction) of the screen.

In the example illustrated in FIG. 4, the time information displayed on the display section 110 is a timeline which includes a time axis 112 and the time values along the time axis. But in another embodiment, as the time information, only a belt-like axis may be displayed on the display section 110 without displaying the figures of time. Or, only the time may be displayed as the time information without displaying an axis. Further, in addition to the display section 110, the time axis 112 can be displayed under the display section 103 to present the timeline.

In the region 201A, multiple signal waveforms obtained from multiple sensors of the same type, or multiple kinds of signal waveforms obtained from multiple kinds of sensors, are displayed in a synchronized manner so that each of the signal waveforms is displayed with the same time axis. For example, the waveforms of the MEG signals obtained from the right side of the head of the subject are displayed side by side on the display section 101, and the waveforms of the MEG signals obtained from the left side of the head of the subject are displayed side by side on the display section 102. In the display section 103, the waveforms of the EEG signals are displayed side by side. These waveforms of the EEG signals represent the voltage measured between the electrodes. Each of the signal waveforms is displayed by correlating with an identification number of the sensor where the signal is obtained or a channel number of the sensor where the signal is obtained.

When the measurement is started and the measured information is collected from each sensor, the signal waveforms are displayed from the left end of each of the display sections 101 through 103 in the region 201A along with the elapse of time. A line 113 represents the measured time (current time), and moves in the screen from left to right. After the signal waveforms are displayed at the right end of the region 201A (the right end of the time axis), the signal waveforms on the screen will be deleted gradually from the left end to the right. Subsequently, new signal waveforms will be displayed from the left side to the right in the location where the signal waveforms are deleted, and the line 113 will move from the left end to the right. Along with the progress of the measurement, in the display section 110 extending in the horizontal direction, the time information on the time axis 112 is updated. The measurement is continued until a stop button 119 is pushed.

One of the characteristics of the present embodiment is that a measurer (recorder) can, during measurement, mark on the point or the range where he/she noticed that there is waveform turbulence, an irregular point of the amplitude, etc., on the signal waveforms. The points or the range to be marked can be designated by the pointing or clicking operation of the mouse. The designated points (or range) on the signal waveforms in the display sections 101 through 103 are highlighted, and the result of the designation is displayed at the time location or the time range corresponding to the designated points (or range) in the display section 110 along the time axis 112. The information of the marked points (or range) including the information displayed in the time axis 112 is recorded with the signal waveform data. The designated point corresponds to a time, and the designated range corresponds to a period of time. Also in the present disclosure, the term "location" may be used as a word meaning both "point" and "range".

In the example illustrated in FIG. 4, a range including one or more channels is designated in the display section 103 at time t1, and a time period including time t1 is highlighted by a mark 103a-1. In connection with the mark 103a-1, an annotation 110a-1 representing the result of the designation is displayed at the time location corresponding to the mark 103a-1 in the display section 110. Also at time t2, another point on the waveform or the vicinity is marked in the display section 103 and a mark 103a-2 is highlighted at the point (time t2) or in the region near time t2 (at least a time range or multiple waveforms are designated). At the same time, an annotation 110a-2 is displayed at the time location corresponding to the mark 103a-2 in the display section 110.

The annotation 110a-1 that was added to the display section 110 at time t1 includes, as an example, an annotation identification number and information about the attribute of the waveforms. In the example illustrated in FIG. 4, an icon representing the attribute of the waveform and the text information of "strong spike" is displayed along with an annotation number "1".

At time t2, when the measurer designates another point on the waveform or the vicinity of the waveform, the mark 103a-2 is highlighted at the designated location. At the same time, an annotation number "2" is displayed at the time location in the display section 110 corresponding to the mark 103a-2. Further, a popup window 115 for selecting an attribute is displayed at the highlighted location. The popup window 115 includes selection buttons 115a for selecting various kinds of attributes, and an input box 115b for inputting comments or additional information. Each of the selection buttons 115a represents the cause of the turbulence of the waveform such as "fast activity", "eye motion", "body motion", "spike", and so on. Since the measurer can check the state of the subject by looking at the monitor window 170 placed in the region 201B on the screen, he/she can appropriately select the attribute representing the cause of the turbulence of the waveform. For example, when a spike occurs in the waveform, he/she can determine if the spike indicates an epileptic syndrome, or if the spike is caused by the body motion (such as a sneeze) of the subject.

FIG. 4 also illustrates similar operation being performed at time t1, in which the selection button 115a representing "spike" was selected; "strong spike" was inputted in the input box 115b, so that the annotation 110a-1 is displayed in the display section 110. Because of this displaying aspect, when multiple signal waveforms are displayed in a synchronized manner so that each of the waveforms is displayed on the same time axis, the point or the range of the signal waveform(s) to be considered can be visually recognized easily, and the basic information of the location to be considered can be grasped easily.

A part or all of the annotation 110a-1, for example, at least one of the attribute icon and the text annotation, may also be displayed near the mark 103a-1 on the signal waveforms in the display section 103. Since the annotation added on the signal waveforms may hinder checking the shape of the waveform, it is desirable that the information displaying system 20 is configured to be selectable by a user (such as a measurer) such that displaying annotations on the signal waveforms in the display sections 101 through 103 is enabled or disabled, if the information displaying system 20 has a function to display annotations on the signal waveforms.

A counter box 118 is for displaying a cumulative number of the spike annotations. Every time "spike" is selected, a counter for the counter box 118 is incremented. Therefore a user can easily recognize the total number of spikes that occurred from the time the measurement was started to the current time (the line 113).

Figure 5:
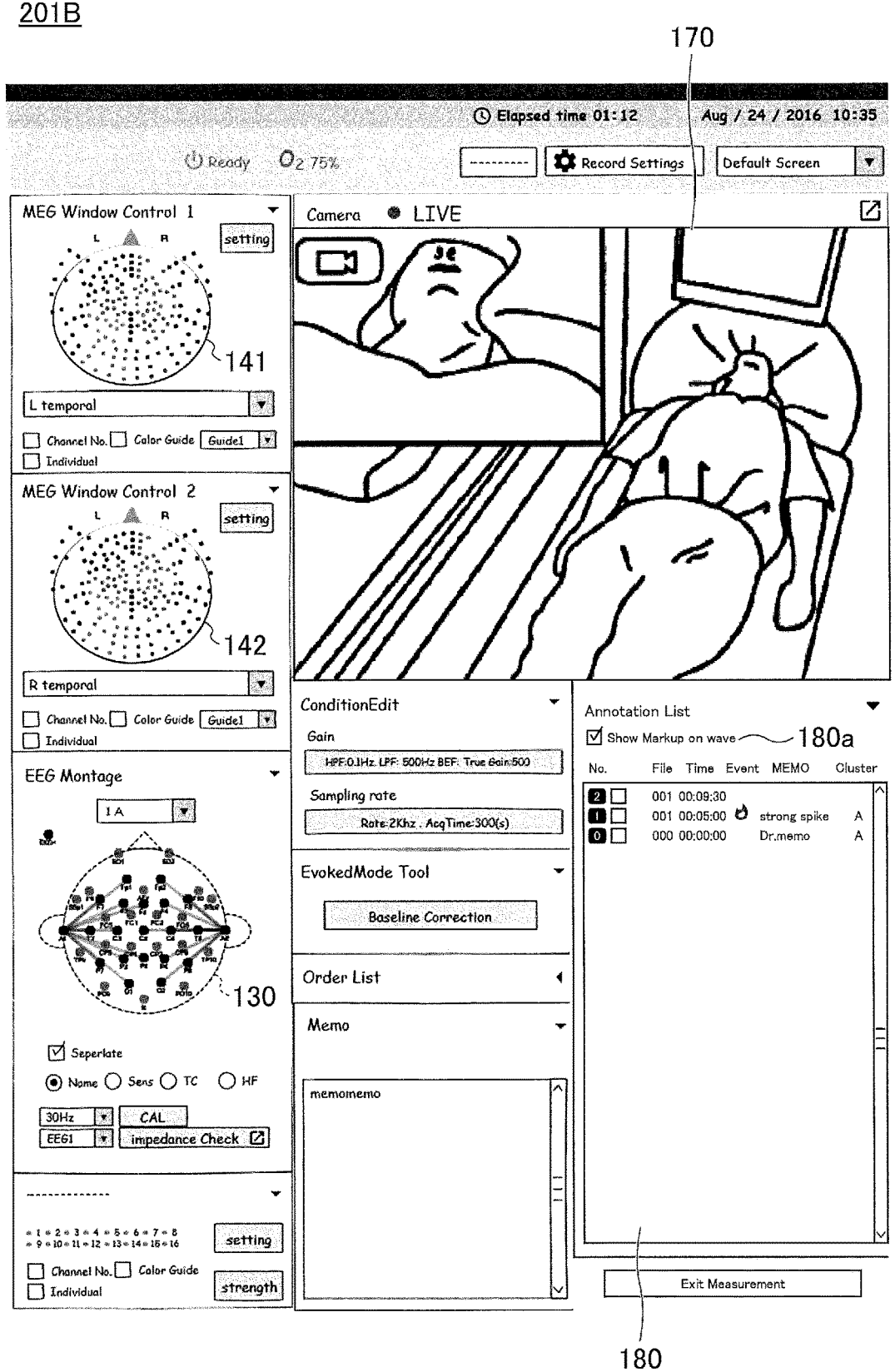
FIG. 5 is an enlarged view of the right region of the measurement screen in FIG. 3.

FIG. 5 is an enlarged view of the right side region 201B of the screen, which illustrates the state of the right side region 201B at the time when the left side region 201A is in the state illustrated in FIG. 4 (when it is the time indicated by the line 113). The monitor window 170 in the region 201B is the window for displaying the live video image of the state of the subject lying on the measurement table 4 with his/her head inserted in the measuring device 3. In the region 201B, distribution maps 141, 142 and 130 and an annotation list 180 are displayed. The distribution maps 141, 142 and 130 correspond to the signal waveforms in the display sections 101, 102 and 103 respectively. The annotation list 180 is the list of the annotations which were marked on the signal waveforms in FIG. 4. Every time a point or a range on the signal waveforms is designated on the display sections 101 through 103 and an annotation is added, the corresponding information is added to the annotation list 180 serially. In the measurement screen, the information added to the annotation list 180 is displayed, for example, in a descending order (e.g., newer information is displayed on the upper row), but the displaying method is not limited to the example. The information in the annotation list 180 may be displayed in the ascending order, but they should be displayed so that the relation between the information and the annotation displayed in the display section 110 along the time axis 112 can be recognized. Further, it is possible to change the order of the information to be displayed, or to sort them by the specific column.

In the example of the annotation list 180 illustrated in FIG. 5, the time information and the added annotation information corresponding to the annotation number "1" is listed. As the annotation information, the attribute icon representing "spike" and the text "strong spike" is recorded. Also, when the mark 103*a*-2 is highlighted, the information corresponding to the annotation number "2" is listed.

A selection box 180*a* is disposed near the annotation list 180 for enabling or disabling to display annotation in the display sections 101 through 103. When the selection box 180*a* is not checked, the annotations other than the highlight mark are not displayed on the display sections 101 through 103, but the annotations in the display section 110 along the time axis 112 are displayed. Because of this function, the annotation information can be recognized without hindering the visibility of the signal waveforms.

Figure 6:
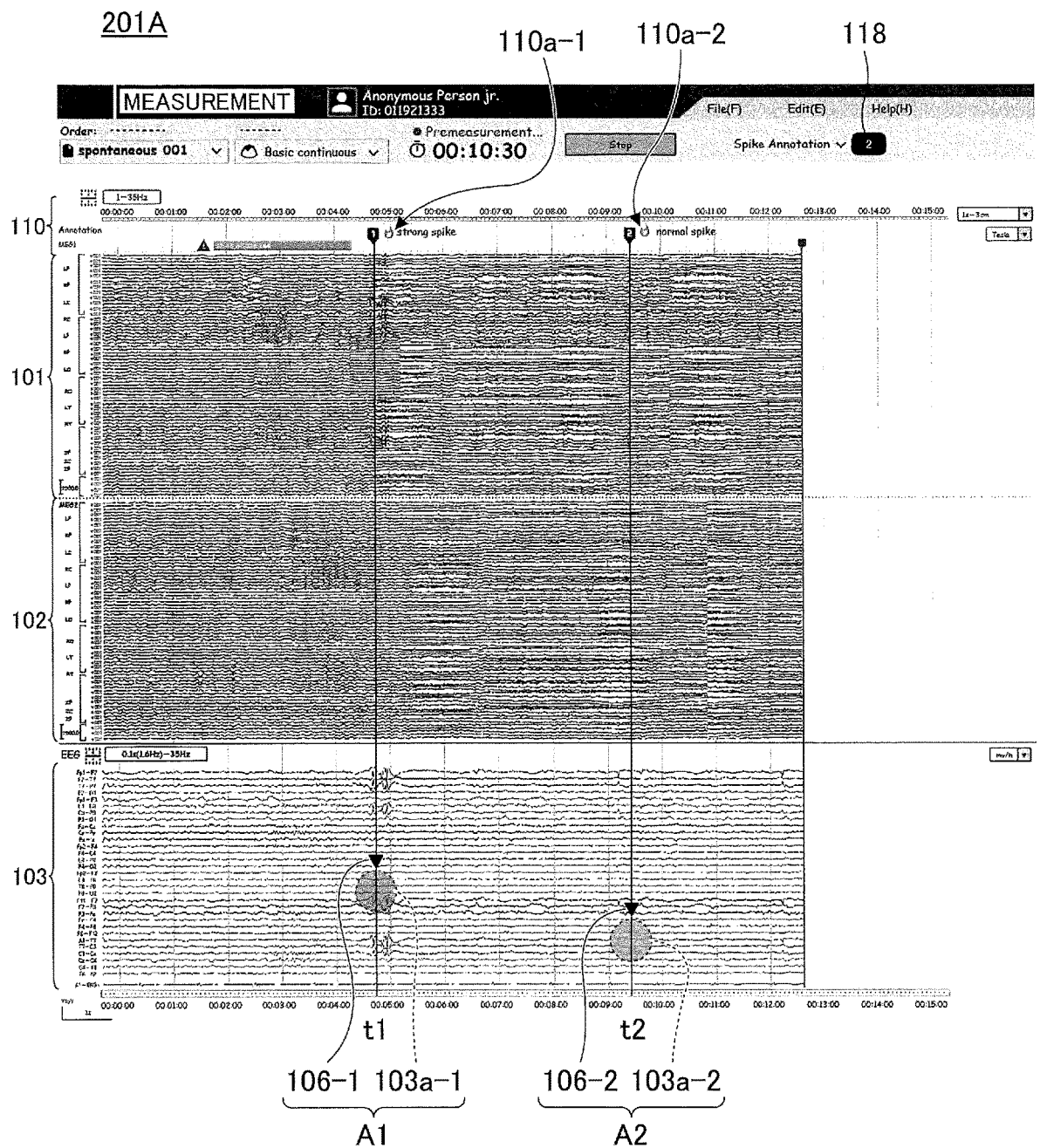
FIG. 6 is a screenshot of a measurement screen just after annotation information is entered.

FIG. 6 illustrates the state of the screen when "spike" is selected in the popup window 115 and the text "normal spike" is inputted in the popup window 115 at time t2. When the "OK" button is pushed in the popup window 115 illustrated in FIG. 4, the popup window 115 closes and the annotation 110*a*-2 is displayed at the corresponding time location in the display section 110, as illustrated in FIG. 6. The attribute icon representing "spike" and the text information "normal spike" are displayed by correlating with the annotation number "2". At the same time, the value of the counter box 118 is incremented. Further, an attribute icon 106-2 is also displayed near the highlighted mark 103*a*-2. In the example illustrated in FIG. 6, an attribute icon 106-1 is displayed near the mark 103*a*-1, but as described above, whether the attribute icons 106-1 and 106-2 should be displayed or not is selectable. An annotation A1 including the mark 103*a*-1 and the attribute icon 106-1, and an annotation A2 including the mark 103*a*-2 and the attribute icon 106-2, are also included in the annotation information.

FIG. 7 illustrates the annotation list 180. When the annotation corresponding to the mark 103*a*-2 is added in the left side region 201A of the screen, the annotation list 180 is updated so that the memo "normal spike" is added to the row of the annotation number "2".

Similarly, every time a point or a range on the signal waveforms is designated during measurement, the designated location is highlighted and the annotation information is displayed along the time axis 112 in the display section 110. In the region 201B, the annotation information is added serially.

It is not necessary to display the annotation number in the annotation list 180 or in the region 201A for displaying the signal waveforms. Any information by which the added annotation can be identified can be used as the identification information. For example, the attribute icon and the attribute text string (such as "strong spike") may be displayed near the time axis by correlating with the time information. Further, a file number (the number that is displayed at the "File" column in the annotation list 180) can also be displayed in the region 201A.

When the stop button 119 (illustrated in FIG. 4) is selected (pushed) and the measurement is finished, the highlighted locations that are designated in the display sections 101 through 103 are recorded by correlating with the signal waveforms. The annotation information that is displayed on the corresponding time location in the display section 110 is also recorded by correlating with the annotation number and the time. The related information, such as the counter value for the counter box 118 and the contents in the annotation list 180, is also recorded. By recording these display information, even if the person who performs analysis is different from the one who performed measurement, the person who performs analysis can easily recognize the problematic location and analyze the signal waveforms at the location.

Figure 8:
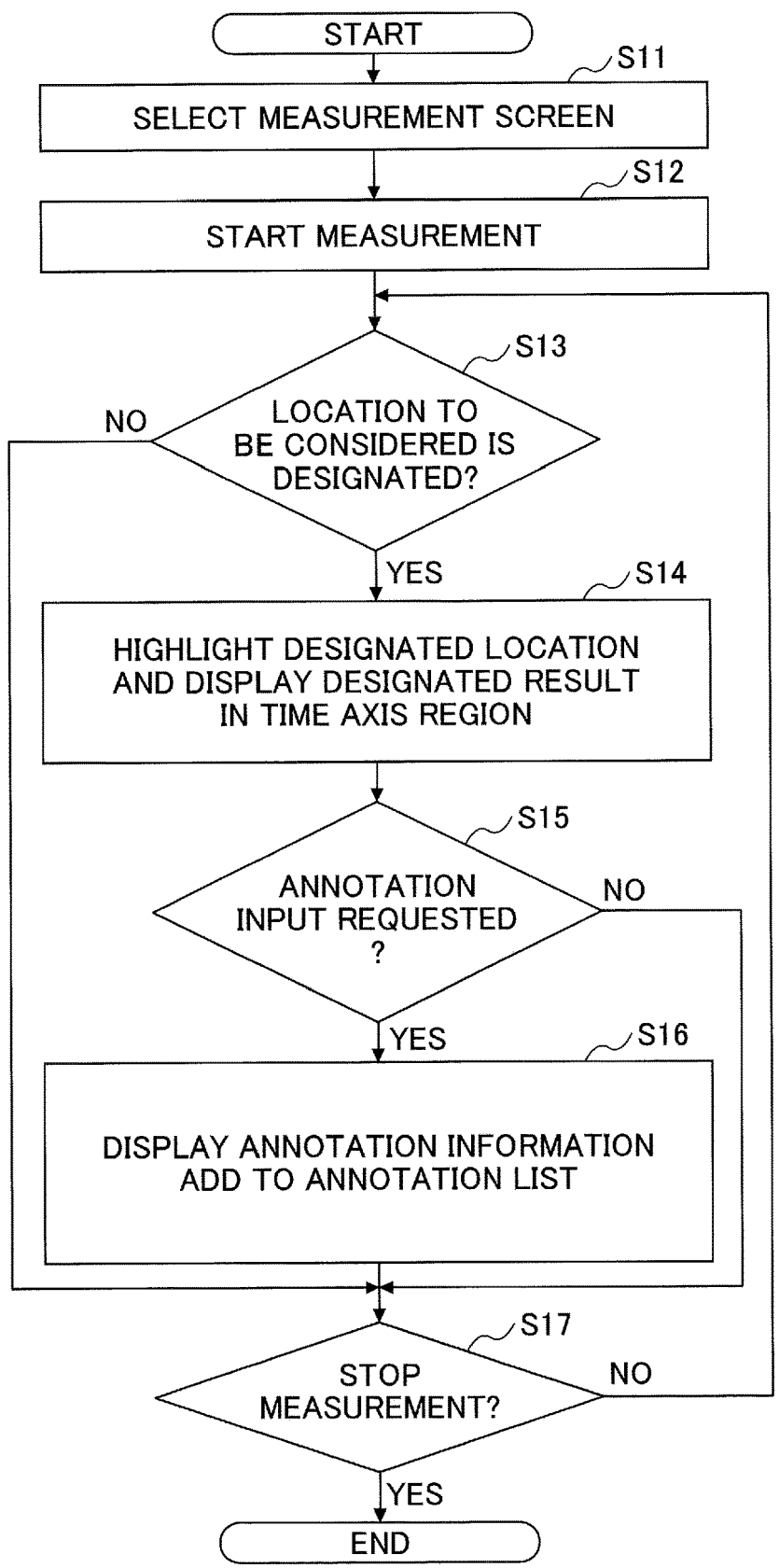
FIG. 8 is a flowchart of the information displaying processing in the measurement phase.

FIG. 8 is a flowchart of the information displaying processing in the measurement phase performed by the information displaying system 20. When "measurement" is selected on the starting screen 204 illustrated in FIG. 2 (S11), the measurement is started and the multiple signal waveforms are displayed in a synchronized manner so that each of the signal waveforms is displayed on the same time axis (S12). Here, "multiple signal waveforms" means both the signal waveforms detected by multiple sensors of the same type and the signal waveforms detected by different types of sensors.

The information displaying system 20 determines whether a designation of a location (point or range) to be considered on the displayed signal waveforms is received or not (S13). When the location to be considered is designated (YES at S13), the information displaying system 20 highlights the designated location in the displaying region of the signal waveforms (display sections 101 through 103) and displays the designated result on the corresponding time location in the time axis region (display section 110) (S14). The designated result includes the information representing that the designation is performed, or the identification information of the designation. At or around the time when the designated result is displayed in the time axis region, the information displaying system determines whether a request for inputting annotation is received or not (S15). If the input of the annotation is requested (YES at S15), the information displaying system 20 displays the received annotation information at the corresponding time location in the time axis region, and adds the annotation information to the annotation list (S16). Subsequently, the information displaying system 20 determines whether a command for requesting the stop of the measurement is received (the stop button 119 is pushed) or not (S17). If the location to be considered is not designated (NO at S13), or if the input of the annotation is not requested (NO at S15), the process proceeds to step S17 and whether the measurement should be terminated or not is determined. Until the measurement finishes (YES at S17), the steps S13 through S16 are executed repeatedly.

According to the information displaying method, the measurement screen which facilitates recognizing the signal information can be provided.

<Operation in the Analysis Phase>

Figure 9:
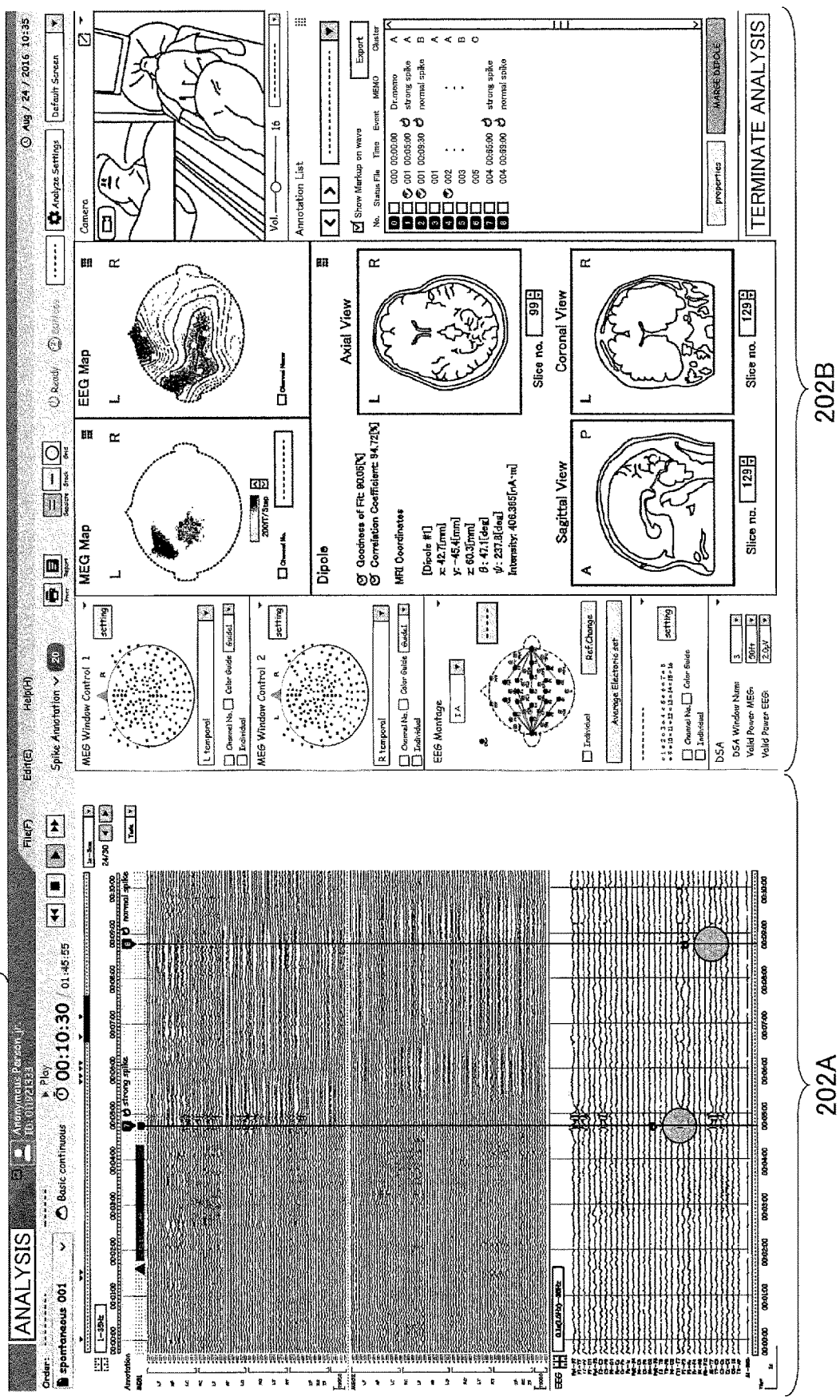
FIG. 9 is an example of an analysis screen.

FIG. 9 illustrates an example of the screen of the information displaying system 20 when analysis is performed. The analysis screen is displayed when the "analysis" button is selected in the starting screen 204 in FIG. 2. There is a label representing that this is the screen for "analysis" on the tab 111 of the analysis screen. The analysis screen includes a region 202A for displaying the recorded signal waveforms with annotations, and a region 202B for displaying analysis information. The region 202A for displaying the recorded signal waveforms and the annotation information is placed on the left side of the screen seen from a user (a measurer or an analyst), and the region 202B for displaying analysis information is placed on the right side of the screen seen from the user. During analysis, since the user checks and finalizes the analysis result on the region 202B using such as a mouse while he/she is checking or selecting the signal waveform(s) on the region 202A, this configuration improves work efficiency of the user.

In the present embodiment, above the second display section 103 for displaying the waveforms of the EEG signals, the second display sections 101 and 102 are placed each of which is for displaying the waveforms of the MEG signals. Also, in the region 202B located at the right of the region 202A, MEG distribution maps 141 and 142 are displayed in the upper part of the region 202B on the side which is closer to the region 202A, and an EEG distribution map 130 is displayed under the distribution maps 141 and 142. Therefore, an analyst can move his/her eyes in the order of the "waveforms of the EEG signals" displayed in the second display section 103, the "waveforms of the MEG signals" displayed in the second display sections 101 and 102, the MEG distribution maps 141 and 142, and the EEG distribution map 130 (in the clockwise order). This makes eye movement of an analyst (or a measurer) efficient, and as a result, the work efficiency of the analysis will be improved. The above description explains the case when the analyst (or the measurer) moves his/her eyes in the clockwise order, but the screen configuration is not limited to the case.

Further in FIG. 9, the case is illustrated that the entire analysis screen is displayed on the screen of the single monitor display 26. Alternatively, the left side region 201A and the right side region 201B may be displayed separately on two or more different monitor displays.

Figure 10:
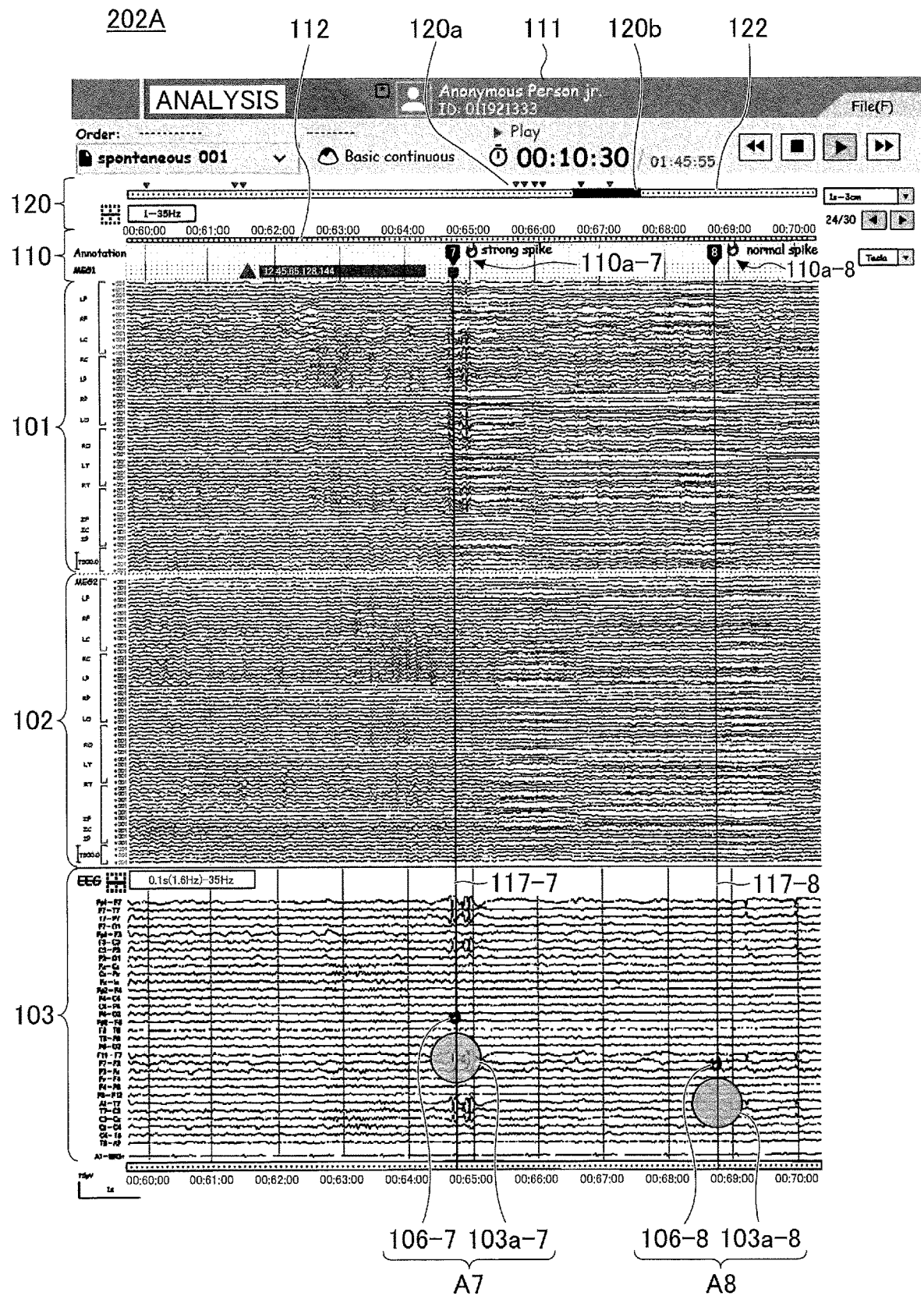
FIG. 10 is an enlarged view of the left region of the analysis screen in FIG. 9.

FIG. 10 is an enlarged view of the left side region 202A of the analysis screen in FIG. 9. The region 202A includes a display section 110 and a display section 120 for displaying the time information in the horizontal direction (first direction) of the screen when the measurement was performed, and the display sections 101 through 103 each of which is for displaying the recorded signal waveforms of one type in parallel so that each of the signal waveforms is arranged in a vertical direction (second direction) of the screen.

The time axis 112, showing the elapse of time during measurement process, is displayed in the display section 110, and the added annotations 110a-7 and 110a-8 are also displayed in the display section 110 along the time axis 112. In the display section 120, a time axis 122 is displayed. The time axis 122 represents the entire period of time when signals were measured and recorded. Along the time axis 122, pointer marks 120a indicating the time location on the signal waveforms where the annotations are added, and a timezone 120b are displayed. The timezone 120b represents the period of time when the signal waveforms that are currently displayed on the display sections 101 through 103 were recorded. By these displayed information, an analyst can intuitively grasp at which phase the signal waveforms which are being analyzed were obtained.

After opening the analysis screen, the analyst can display a desired part of the signal waveforms on the display sections 101 through 103 by, for example, dragging the timezone 120b on the time axis 122. Or, as will be described later, by selecting one of the desired annotations, part of the signal waveforms including the selected annotation can be displayed on the display sections 101 through 103.

Annotations A7 and A8 which were added during measurement are displayed on the display sections 101 through 103. Marks 103a-7 and 103a-8 are highlighted, and attribute icons 106-7 and 106-8 corresponding to the marks 103a-7 and 103a-8 are displayed near the marks 103a-7 and 103a-8. Further, vertical lines 117-7 and 117-8 each of which indicates the time location of the marks 103a-7 and 103a-8 are displayed. By displaying the line 117, for example, when a certain location in the display section 103 is designated and an annotation relating to the location is added, the result of the designation can be easily recognized in the display section 102 or 101 which are different types of the signal displaying area from the display section 103. Since the line 117 makes the visual recognition of the annotation information easier, it can be included in the annotation information, and it may be called "annotation line". By selecting one of the lines 117, the signal waveforms for the fixed period of time before and after the time indicated by the selected line 117 is displayed with magnification. The processing will be described later.

Figure 11:
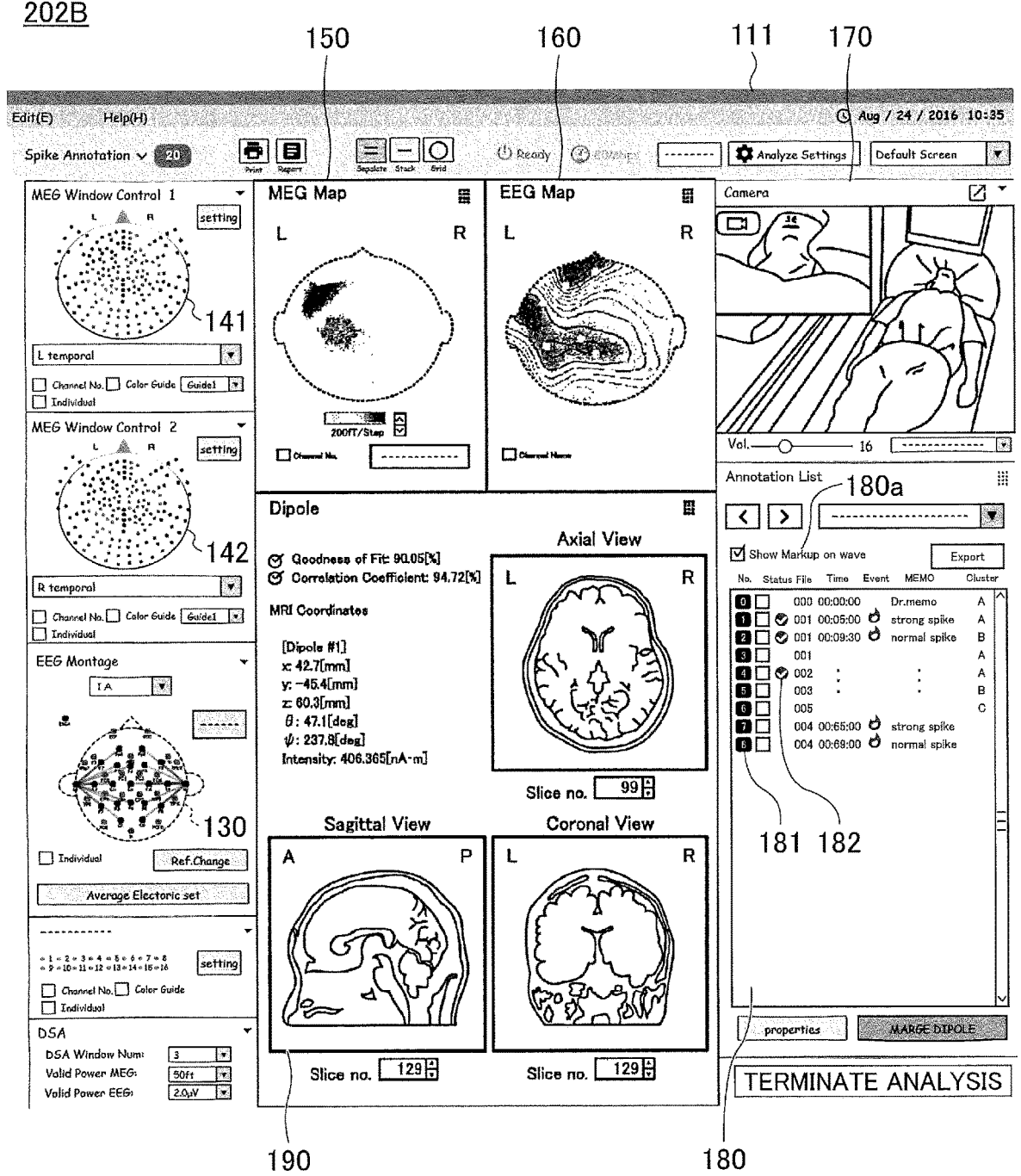
FIG. 11 is an enlarged view of the right region of the analysis screen in FIG. 9.

FIG. 11 is an enlarged view of the right side region 202B of the screen, which illustrates the state of the region 202B at the time when the region 202A is in the state illustrated in FIG. 10. In the right side region 202B, MEG distribution maps 141 and 142 each corresponding to the signal waveforms displayed on the display sections 101 and 102, and the EEG distribution map 130 corresponding to the signal waveforms displayed on the display section 103, are displayed. Also, an isomagnetic field diagram 150 of the magnetoencephalogram (MEG), a map area 160 of the electroencephalogram (EEG), and a displaying window 190 for displaying brain tomographic images of the subject obtained by MRI (Magnetic Resonance Imaging) are displayed in the right side region 202B. On the isomagnetic field diagram 150, a magnetic flux source and a magnetic flux sink are drawn by different colors so that the direction of current can be visually grasped. The diagrams drawn in the isomagnetic field diagram 150 and the map area 160 are obtained after the measurement process described earlier was finished, and the MRI tomographic images are obtained by another measurement.

On the monitor window 170, the video image of the subject taken when his/her measurement was made is displayed in synchronization with the display of the signal waveforms on the display sections 101 through 103. By watching the monitor window 170, an analyst can analyze the signal waveforms by checking the state of the subject.

All of the annotations which were added during the measurement phase are listed in the annotation list 180. In the annotation list 180, the annotation information (attribute icon, input text information, and the like) which was added during the measurement phase is recorded by correlating with an annotation number 181. On the annotation list 180 in the analysis screen, for example, each of the annotations is displayed in an ascending order (older annotation is placed in the upper row), but the displaying order is not limited to the example described here. Similar to the annotation list illustrated in the measurement screen, it is not necessary to use an annotation number. Each annotation may be distinguished from each other by the combination of time, filename, attribute, and the like. The information displaying system 20 may also be configured that a user can change the order of the annotations to be displayed in the annotation list 180, or sort each of the annotations by the specific column. By clicking the desired annotation number 181 or the desired row in the annotation list 180, the signal waveforms for a certain time period including the time location on the signal waveforms for which the clicked annotation was added are displayed on the display sections 101 through 103 in FIG. 10.

When an analyst checks the signal waveforms in a region where an annotation was attached and estimation of the signal source based on the signal waveforms in the region is performed, the annotation is displayed with an estimation completion mark 182 (as will be illustrated in FIG. 11) attached, which is different from the annotation list in the measurement screen.

When an analyst chooses not to display an annotation in the display sections 101 through 103 using the selection box 180a, the attribute icons 106-7 and 106-8 disappear on the display section 103 in FIG. 10. The information displaying system 20 may also be configured such that a user can select whether the highlighted marks 103a-7 and 103a-8 are displayed or not using the selection box 180a.

Figure 12:
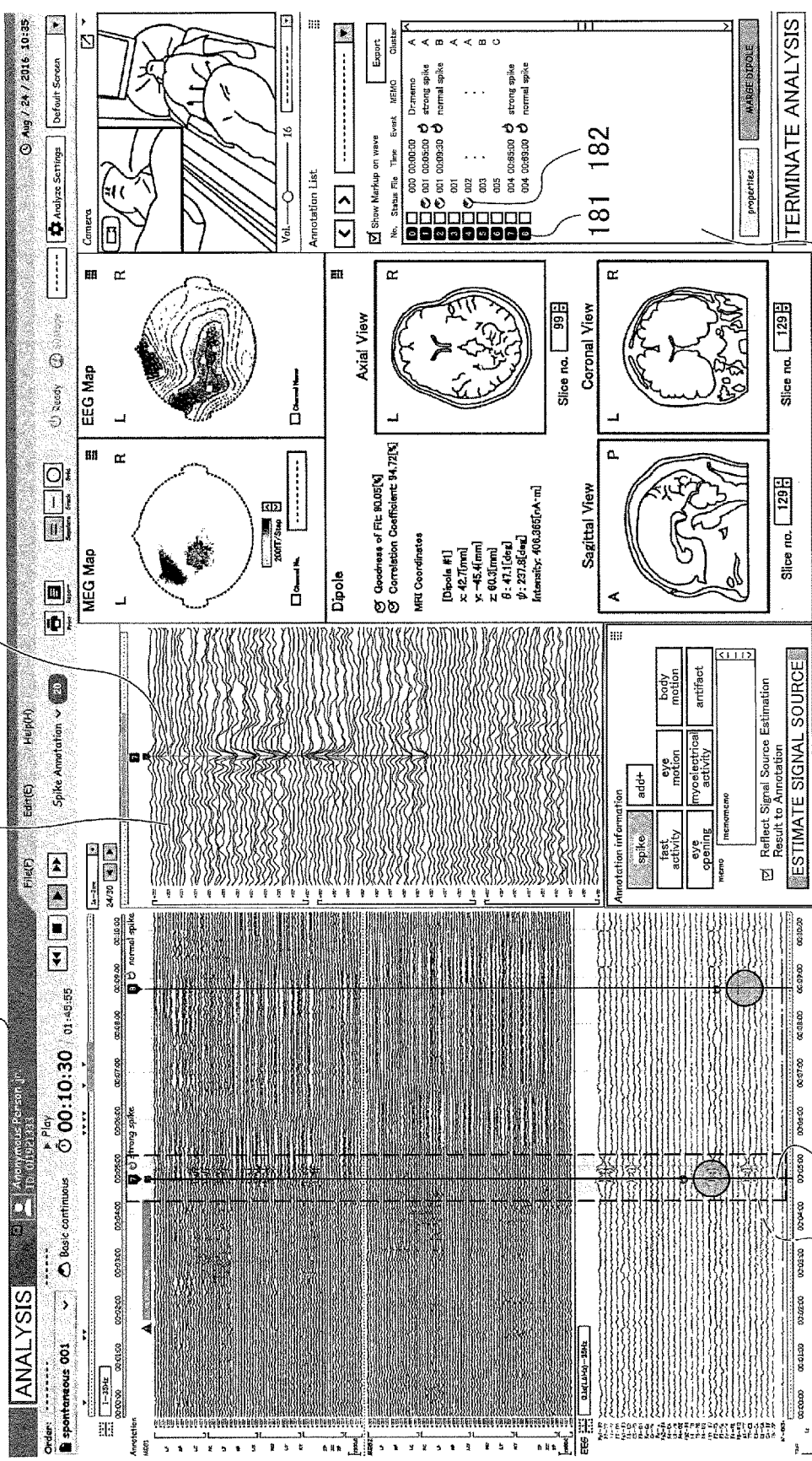
FIG. 12 is a screenshot of the analysis screen in FIG. 10 just after one of the annotation lines is selected.

FIG. 12 is the view of the analysis screen illustrating the state just after the line 117-7 in FIG. 10 is selected (the line 117-7 can be selected, for example, when an analyst double-clicks the line 117-7 using a mouse). When an analyst notices the annotation A7 and selects (performs double-click operation, for example) the line 117-7 to analyze the waveforms in the location (region) indicated with the annotation A7, the signal waveforms in the vicinity of the highlighted signal waveforms are displayed with magnification in a magnified view area 200. The signal waveforms included in the fixed period of time specified with the region 114 are magnified and displayed with a line 217-7 indicating the time location when the annotation A7 was added.

Figure 13:
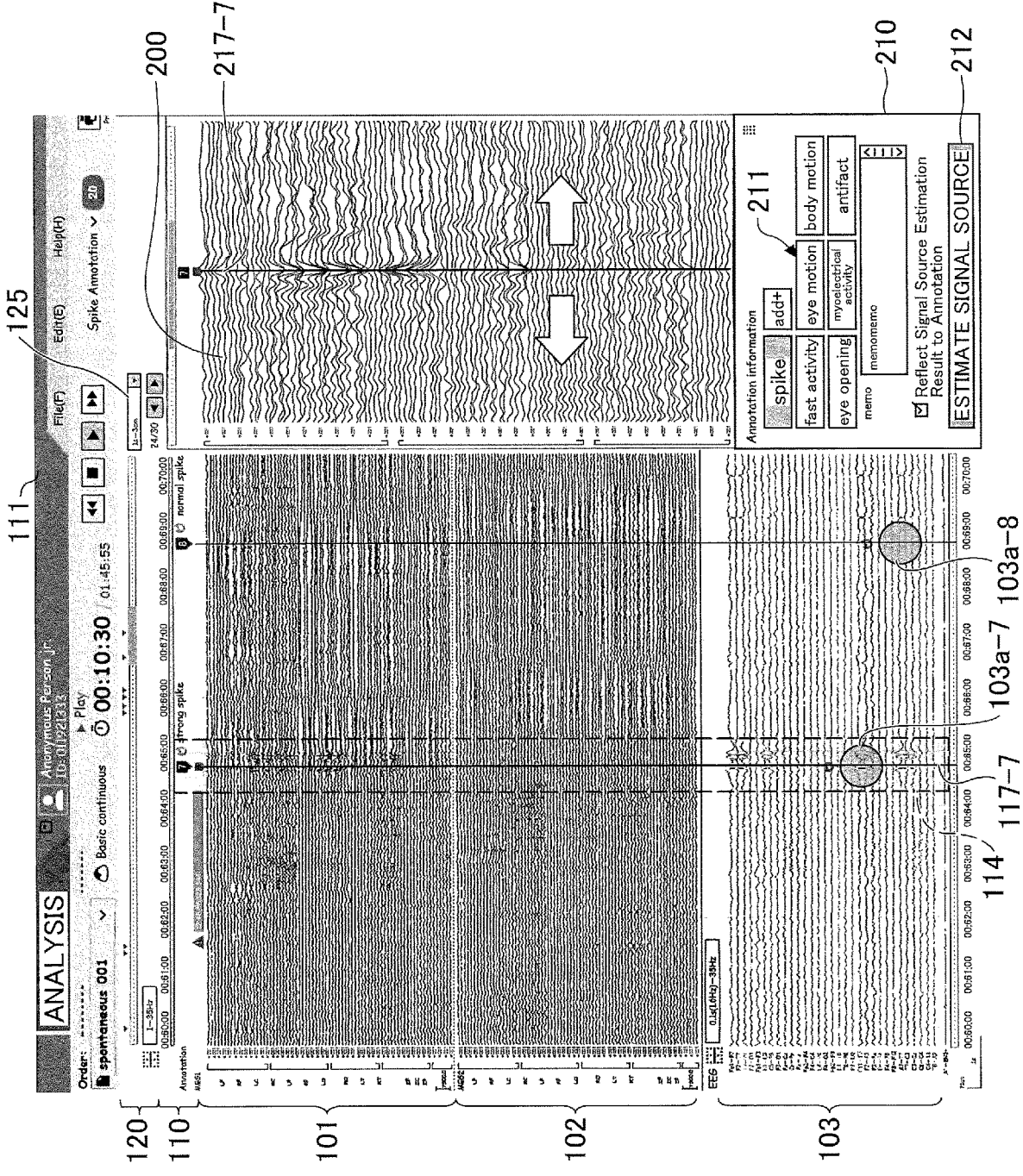
FIG. 13 is an enlarged view of the left region of FIG. 12.

FIG. 13 is the enlarged view of a region 203A (signal waveform displaying region) which is located at the left side in FIG. 12. An analyst can double-check whether the mark added during measurement phase is appropriate or not, or can check a part of the waveforms which was not checked during measurement phase, by displaying the signal waveforms with magnification in the magnified view area 200. For example, by dragging the line 217-7 to the left or right, the analyst can detect the accurate location in the waveforms where there is a problem, or change the location where the annotation is to be added. The information displaying system may be configured that at least one of the highlighted mark 103a and the attribute icon 106 displayed in the display section 103 are also displayed in the magnified view area 200. However, since the highlighted mark or the attributed icon may hinder determining an irregular point of the amplitude correctly when viewing the waveforms, it is desirable that the information displaying system 20 is configured to be selectable by a user such that displaying the highlighted mark or the attributed icon in the magnified view area 200 is enabled or disabled.

The type of the signal waveforms or the channel range of the signal waveforms to be displayed on the magnified view area 200 may be selectable. For example, an analyst glances from the highlighted mark 103a-7 in the display section 103 to the upper region in the screen, to check if there is an irregular point of the amplitude in the waveforms displayed in the display section 101 or 102 where the waveforms of the MEG signals are displayed. In this case, by entering, in a box 125, the channel range of the signal waveforms that he/she wants to magnify, among the waveforms in the display section 101 or 102, the waveforms of the MEG signals related to the mark 103a-7 can be displayed in the magnified view area 200.

A confirmation window 210 is displayed under the magnified view area 200. The confirmation window 210 includes signal waveform attribute buttons 211 and a signal source estimation button 212. The attribute buttons 211 are similar to the selection buttons 115a, and when the attribute which was added during measurement is incorrect, an analyst can alter the attribute to an appropriate one by selecting an appropriate attribute button 211. After the analyst confirms that the location of the signal waveforms to be considered and/or the selected attribute are appropriate, he/she clicks the signal source estimation button 212 to reflect the estimated result of a signal source to the annotation.

Figure 14:
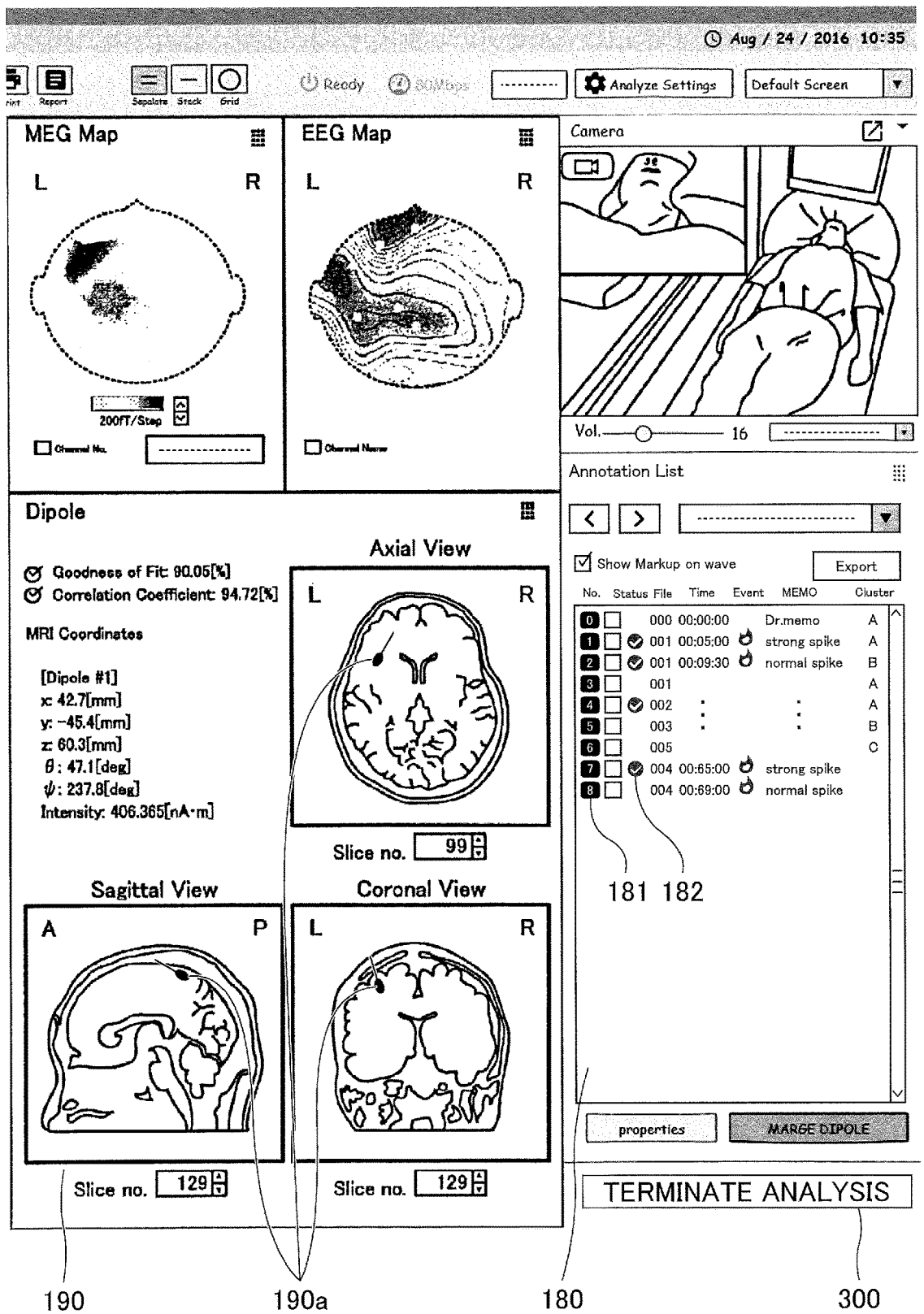
FIG. 14 is an enlarged view of the right region of FIG. 12.

FIG. 14 is an enlarged view of the right side region 203B in FIG. 12. When an analyst confirms the appropriateness of the location of the signal waveforms to be considered and/or the selected attribute related to the selected annotation, and pushes the signal source estimation button 212 by using the screen illustrated in FIG. 13, the estimation completion mark 182 is added to the row corresponding to the selected annotation in the annotation list 180 (in the example illustrated in FIG. 14, the estimation completion mark 182 is added to the annotation whose annotation number is "7"). Further, an estimated result of a dipole 190a is displayed on the MRI tomographic images in the displaying window 190.

There are two approaches for updating the annotation list 180 when an analyst changes at least one of the location of a mark which is highlighted in the display sections 101 through 103 and the contents of an annotation 110a. One approach is to record, in the annotation list 180, only the latest information which was updated by the analyst, and the other approach is to add the information which was updated by the analyst to the annotation list 180 while keeping the annotation information which was recorded in the measurement phase. If the latter approach is adopted, a new annotation number may be given to the added annotation information as annotation identification information. For example, the new annotation number may be made by adding a branch number to the annotation number which was given to the original annotation information at the measurement phase. In this case, the added annotation may also be displayed on the display section 110, and the added annotation information may be displayed along the time axis with a different color from the original annotation information.

Figure 15:
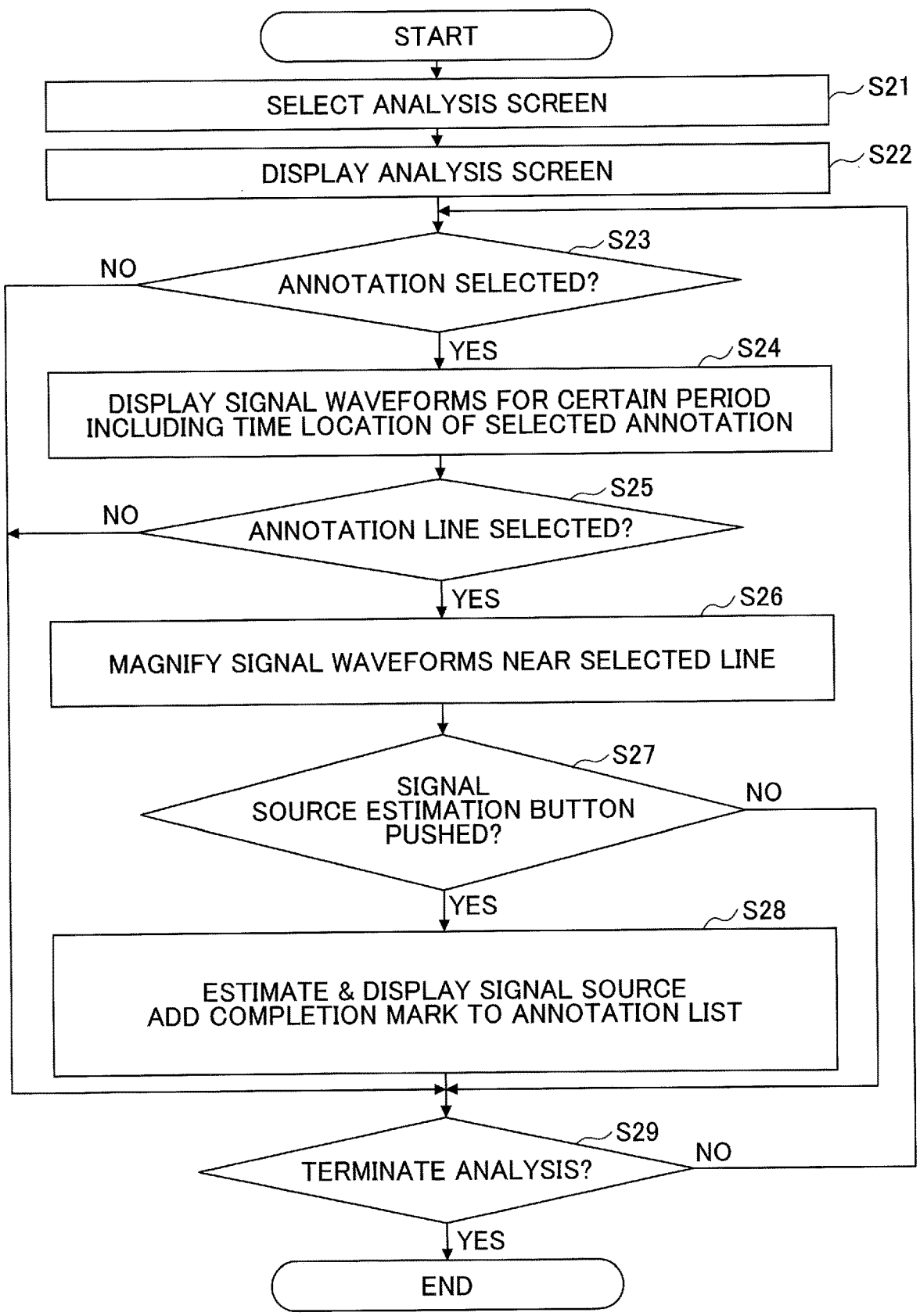
FIG. 15 is a flowchart of the information displaying processing in the analysis phase.

FIG. 15 is a flowchart of the information displaying processing in the analysis phase performed by the information displaying system 20. When "analysis" is selected on the starting screen 204 (see FIG. 2) (S21), the analysis is started and the analysis screen is displayed (S22). The analysis screen initially may be a blank screen where no signal waveform is displayed, or the signal waveforms measured in the fixed period of time after starting the measurement or before completion of the measurement may be displayed on the analysis screen. When the analysis screen is displayed, the information displaying system 20 determines whether a certain annotation was selected or not (S23). The annotation may be selected by choosing an annotation number or a row in the annotation list 180, or may be selected by designating the time location using the timezone 120b which is displayed on the time axis 122 in the display section 120. When a selection of the annotation has occurred (YES at S23), the signal waveforms within the certain period including the time location where the selected annotation is attached are displayed (S24).

After the signal waveforms are displayed, the information displaying system 20 determines whether a line 117 representing the time location where the highlighted mark exists is selected or not (S25). When the line 117 is selected (YES at S25), the signal waveforms within the fixed period of time including the time indicated by the selected line 117 are displayed with magnification (S26). The signal waveforms that are magnified and displayed here are not limited to the signal waveforms near the highlighted mark. Instead, another type of the signal waveforms within the same time location as the highlighted mark may be displayed with magnification. For example, if a highlighted mark is added to the waveforms of the EEG signals, the waveforms of the MEG signals at the same time location as the highlighted mark may be displayed with magnification. Or, instead of displaying the signal waveforms of all channels, only the signal waveforms obtained from the fixed range of channels including the channel from which the marked signal waveforms was obtained may be displayed with magnification. In these cases, the information displaying system 20 may determine whether the types of the signal waveforms to be displayed are designated or not, or whether the range of the channels from which the signal waveforms to be displayed was obtained is designated or not.

Next, whether the signal source estimation button 212 was pushed or not is determined (S27). If the signal source estimation button 212 was pushed (YES at S27), the information displaying system 20 performs calculation to estimate the signal source. The estimated result is displayed on the MRI tomographic images, and the estimation completion mark 182 is added to the annotation list 180 (S28). Then, whether the command for instructing to terminate analysis was received or not (whether "terminate analysis" button 300 illustrated in FIG. 14 is pushed or not) is determined (S29). If no annotation was selected (NO at S23), if the annotation line was not clicked (NO at S25), or if the signal source estimation button 212 was not pushed (NO at S27), the process proceeds to S29 and the information displaying system 20 determines whether the analysis should be terminated or not. Until the command for instructing to terminate analysis is received (YES at S29), the steps S23 through S28 are repeated.

Between step S26 and step S27, the information displaying system 20 may perform a determination process as to whether the annotation was changed or not. If the annotation was changed, the information displaying system 20 reflects the change to the annotation list 180 and proceeds to the determination at step S27.

Because of the above displaying processing, the information displaying system 20 can realize the information displaying method excellent in visibility and operability.

Figure 16:
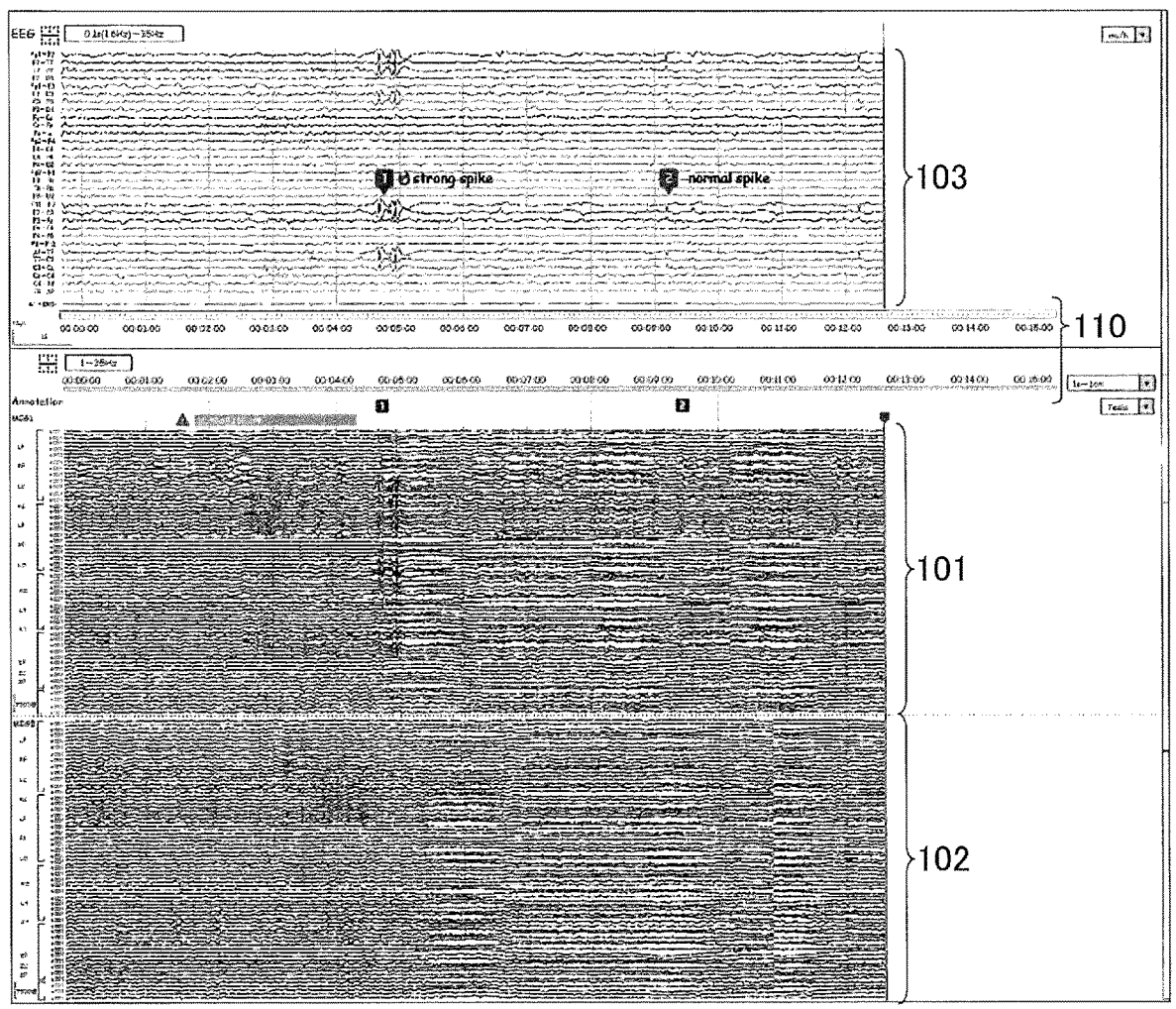
FIG. 16 is a diagram illustrating a modified example of the display layout.
Figure 17:
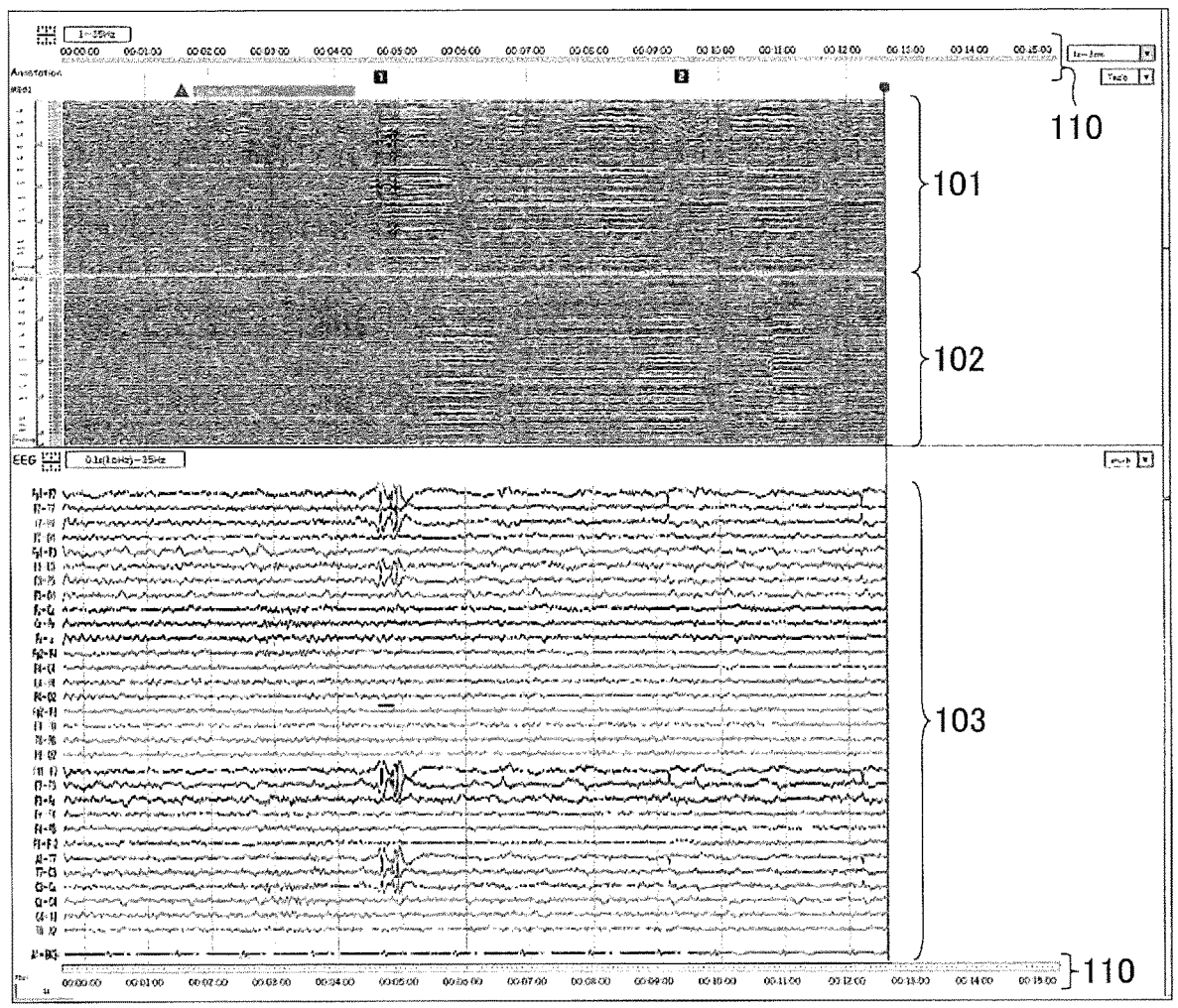
FIG. 17 is a diagram illustrating another modified example of the display layout.

FIG. 16 and FIG. 17 are the diagrams illustrating a modified example of the display layout. In displaying the signal waveforms obtained from multiple types of sensors, a user can change the display location of each signal waveform based on the type of the signals accordingly. For example, as illustrated in FIG. 16, the display section 103, which illustrates the waveforms of the EEG signals having a large amplitude and easy to recognize, may be placed in the upper part of the screen. In this case, the MEG distribution maps 141 and 142 are placed at the right side of the display sections 101 and 102, and the EEG distribution map 130 is placed at the right side of the display section 103 and above the MEG distribution maps 141 and 142. Further, as illustrated in FIG. 17, the information displaying system 20 may be configured that the vertical size of at least one of the display sections 101 through 103 can be changed. For example, when a user selects the frame of the display section 103 and moves the frame vertically, the ratio of the size of the display section 103 to the vertical size of the display section 101 or 102 can be changed.

The location of the display section 110 for displaying a timeline may not necessarily be the upper end of the screen or the lower end of the screen. The display section 110 may be placed between the waveforms of the MEG signals and the waveforms of the EEG signals. Further, for example, both the configuration in which the timeline is placed between the waveforms of the MEG signals and the waveforms of the EEG signals and the configuration in which the timeline is placed at at least one of the upper end and the lower end of the screen may be adopted.

Figure 18:
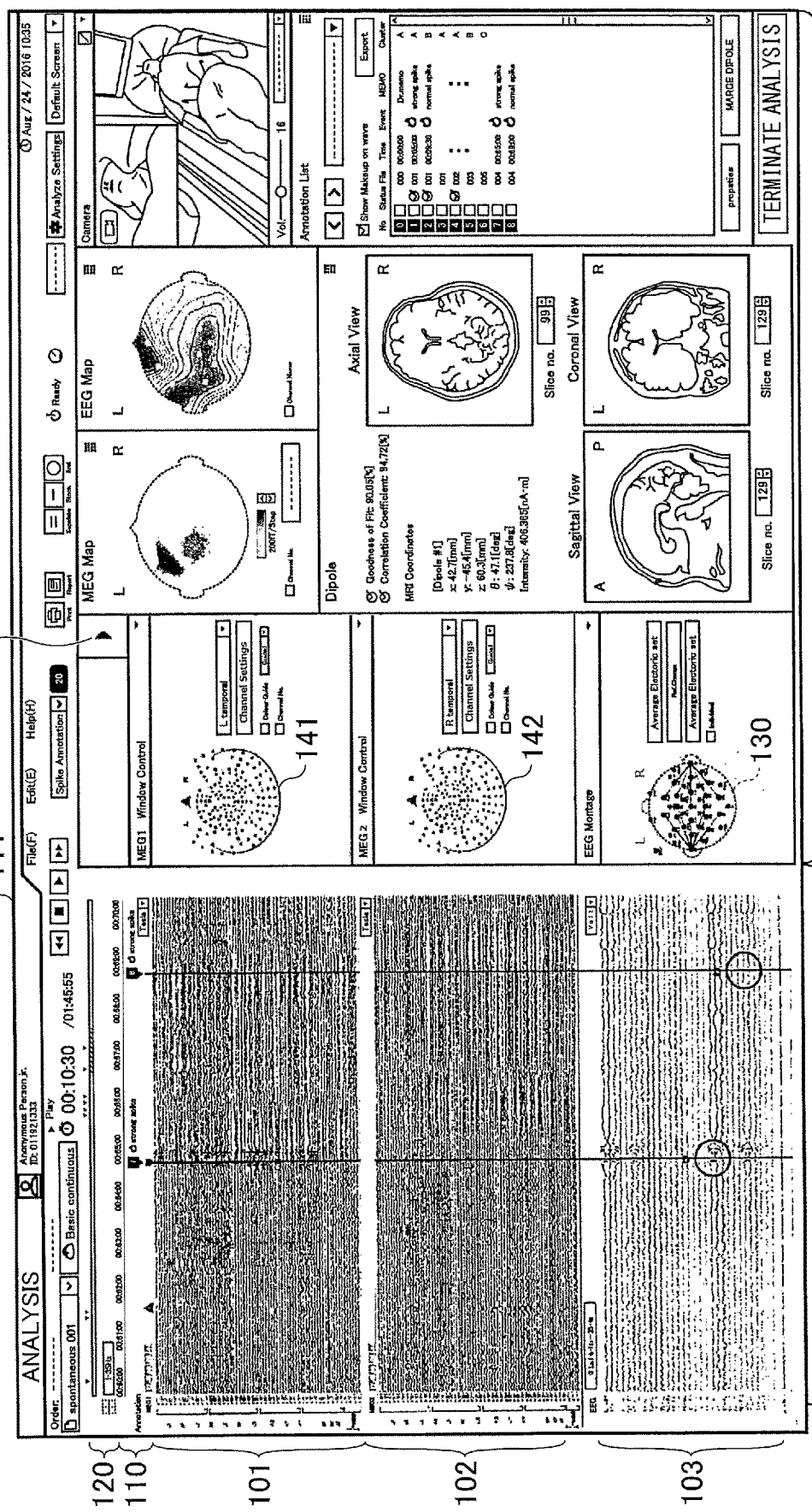
FIG. 18 is a diagram illustrating a modified example of the analysis screen illustrated in FIG. 9.
Figure 19:
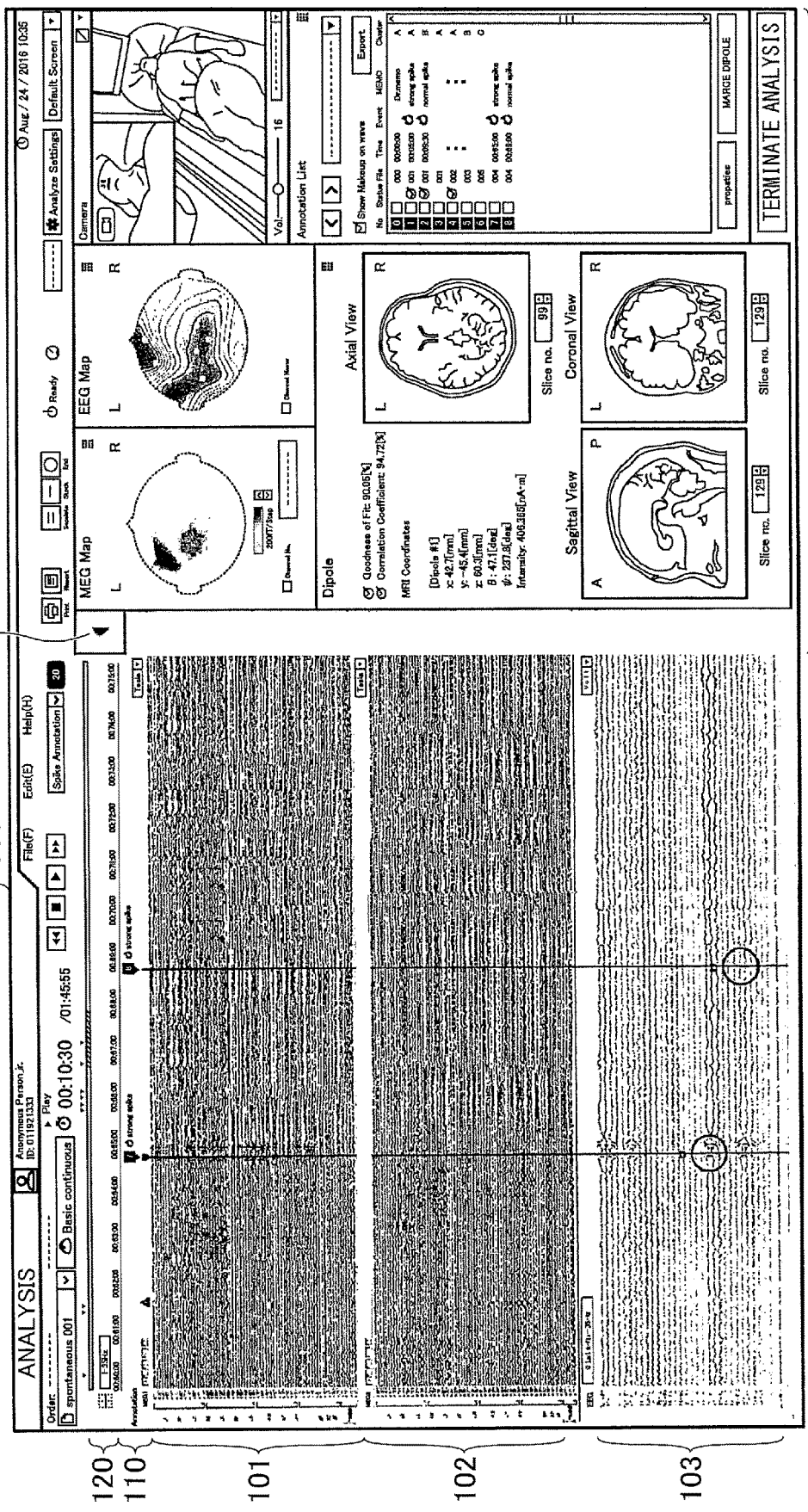
FIG. 19 is a diagram illustrating a modified example of the analysis screen illustrated in FIG. 9.

FIG. 18 and FIG. 19 are the diagrams illustrating a modified example of the analysis screen. In the example illustrated in FIG. 18, the positional relation of the distribution maps and the display sections is different from the example illustrated in FIG. 9. As illustrated in FIG. 18, the distribution map 141 and the display section 101 for displaying MEG signal waveforms are displayed adjacent to each other, the distribution map 142 and the display section 102 for displaying MEG signal waveforms are displayed adjacent to each other, and the distribution map 130 and the display section 103 for displaying EEG signal waveforms are displayed adjacent to each other. This screen configuration improves the visibility as compared to the screen configuration illustrated in FIG. 9 since a user can easily recognize the distribution map corresponding to the waveforms in a display section that he/she is observing only by moving his/her eyes horizontally from the waveforms to the corresponding distribution maps.

In the example illustrated in FIG. 18, a switch button 143 for expanding the display sections is displayed above the distribution map 141. A symbol representing the direction (the rightward in FIG. 18) in which the region 202A for displaying the waveforms and the annotations is expanded by pushing the switch button 143 is labeled on the switch button 143. When the switch button 143 is pushed, as illustrated in FIG. 19, the region 202A is expanded horizontally and the waveforms are displayed on the expanded region 202A. Therefore, the waveforms for a longer period of time can be displayed as compared to the display section illustrated in FIG. 9. When a user pushes the switch button 143 on the screen illustrated in FIG. to restore the size of the region 202A, the region 202A returns to the state illustrated in FIG. 18. On the switch button 143 illustrated in FIG. 19, a symbol representing the direction (the leftward in FIG. 19) in which the region 202A for displaying the waveforms shrinks by pushing the button 143 is labeled. As described above, since the symbol labeled on the switch button 143 indicates the direction in which the size of the display sections is changed, a user can easily grasp whether the display sections 101 through 103 will be expanded or shrink, and the usability is improved.

Figure 20:
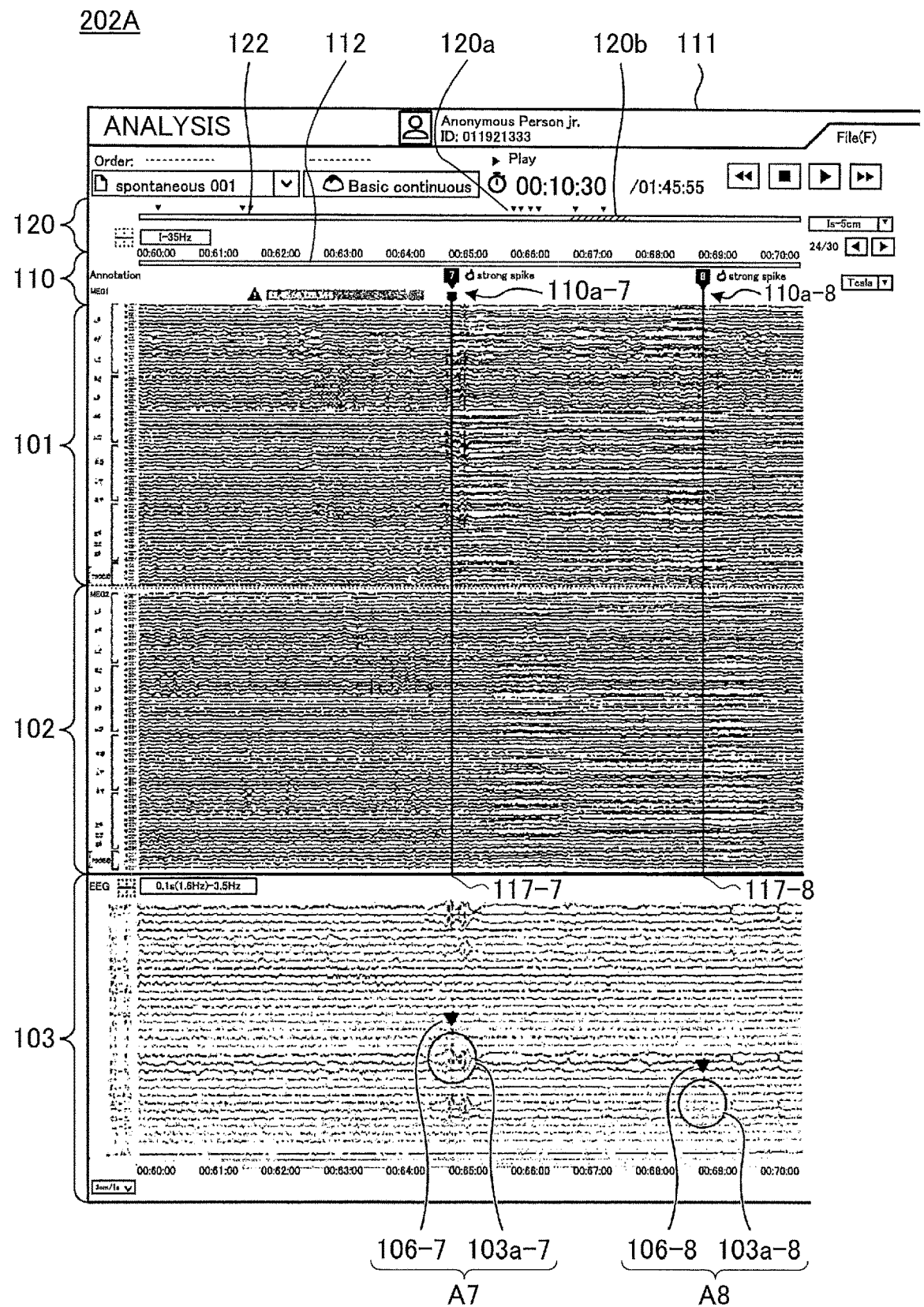
FIG. 20 is a diagram illustrating a modified example of FIG. 10.

FIG. 20 is a diagram illustrating a modified example of the analysis screen as illustrated in FIG. 10. In FIG. 20, the lines 117-7 and 117-8 are not displayed on the display section 103 where annotations are displayed, but are displayed on the display sections 101 and 102, which is different from the analysis screen illustrated in FIG. 10.

In the display sections 101 through 103, annotations A7 and A8 which were added to the signal waveforms during measurement are displayed. Marks 103a-7 and 103a-8 are highlighted and the attribute icons 106-7 and 106-8 each corresponding to the marks 103a-7 and 103a-8 are displayed near the marks 103a-7 and 103a-8. Further, the vertical lines 117-7 and 117-8 each of which represents the time location of each mark 103a-7 and 103a-8 are displayed only in the display sections 101 and 102.

According to the example, an analyst can, by moving his/her eyes from the highlighted mark 103a-7 in the display section 103 to the upper region of the screen, check if there is an irregular point of the amplitude in the waveforms displayed in the display section 101 or 102 where the waveforms of the MEG signals are displayed.

Figure 21:
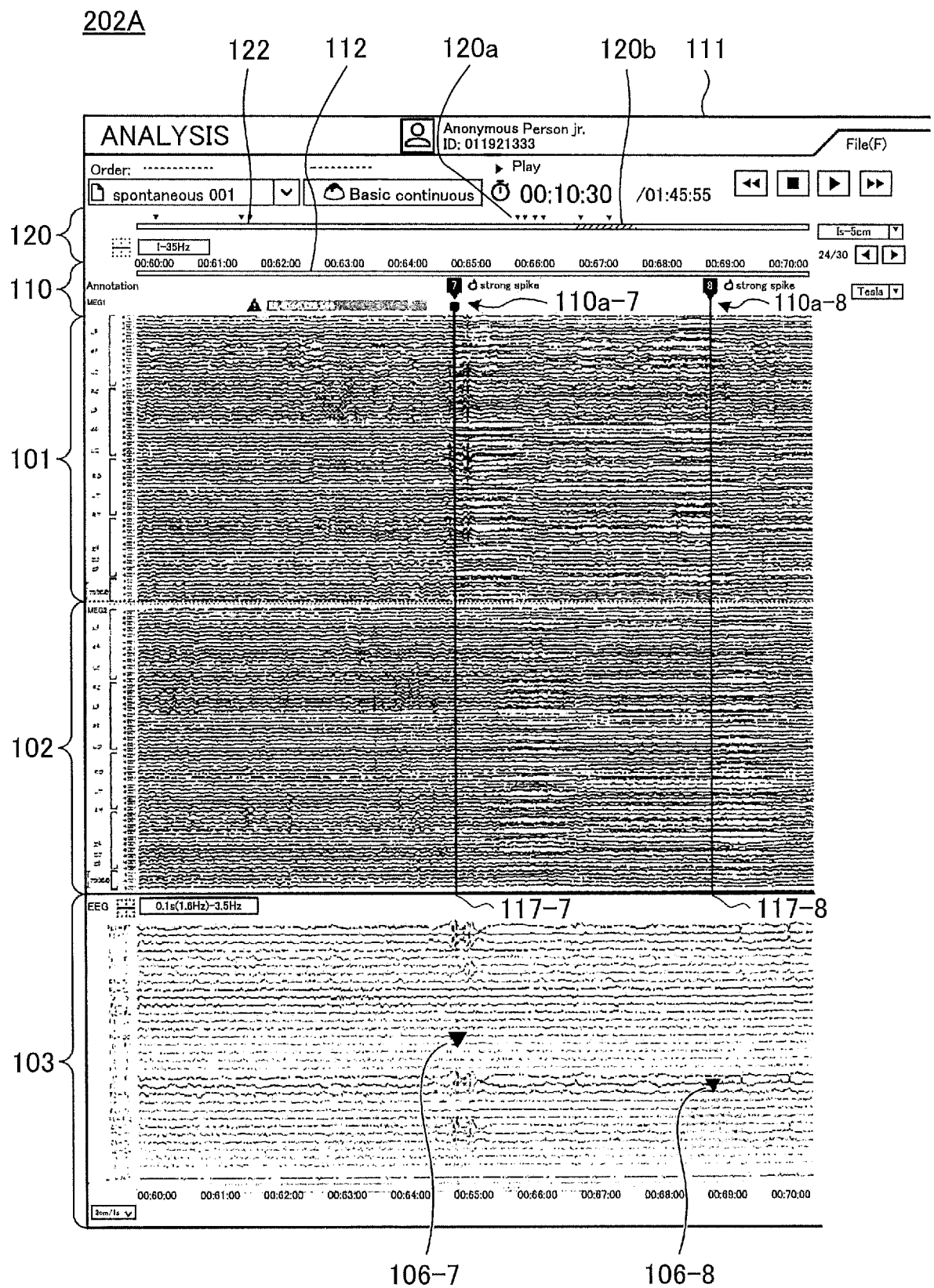
FIG. 21 is a diagram illustrating a modified example of FIG. 10.

FIG. 21 is a diagram illustrating another modified example of the analysis screen as illustrated in FIG. 10. In the display sections 101 through 103, annotations which were added to the signal waveforms during measurement are displayed. In the example illustrated in FIG. 21, attribute icons 106-7 and 106-8 are displayed on the location where irregular points on the waveform were designated in the display section 103. The attribute icons 106-7 and 106-8 indicate the designated locations and attributes. Also, the vertical lines 117-7 and 117-8 each of which represents the time location of each attribute icon 106-7 and 106-8 are displayed only in the display sections 101 and 102.

Also according to the example, an analyst can, by moving his/her eyes from the attribute icons 106-7 and 106-8 in the display section 103 to the upper region of the screen, check if there is an irregular point of the amplitude in the waveforms displayed in the display section 101 or 102 where the waveforms of the MEG signals are displayed.

Figure 22:
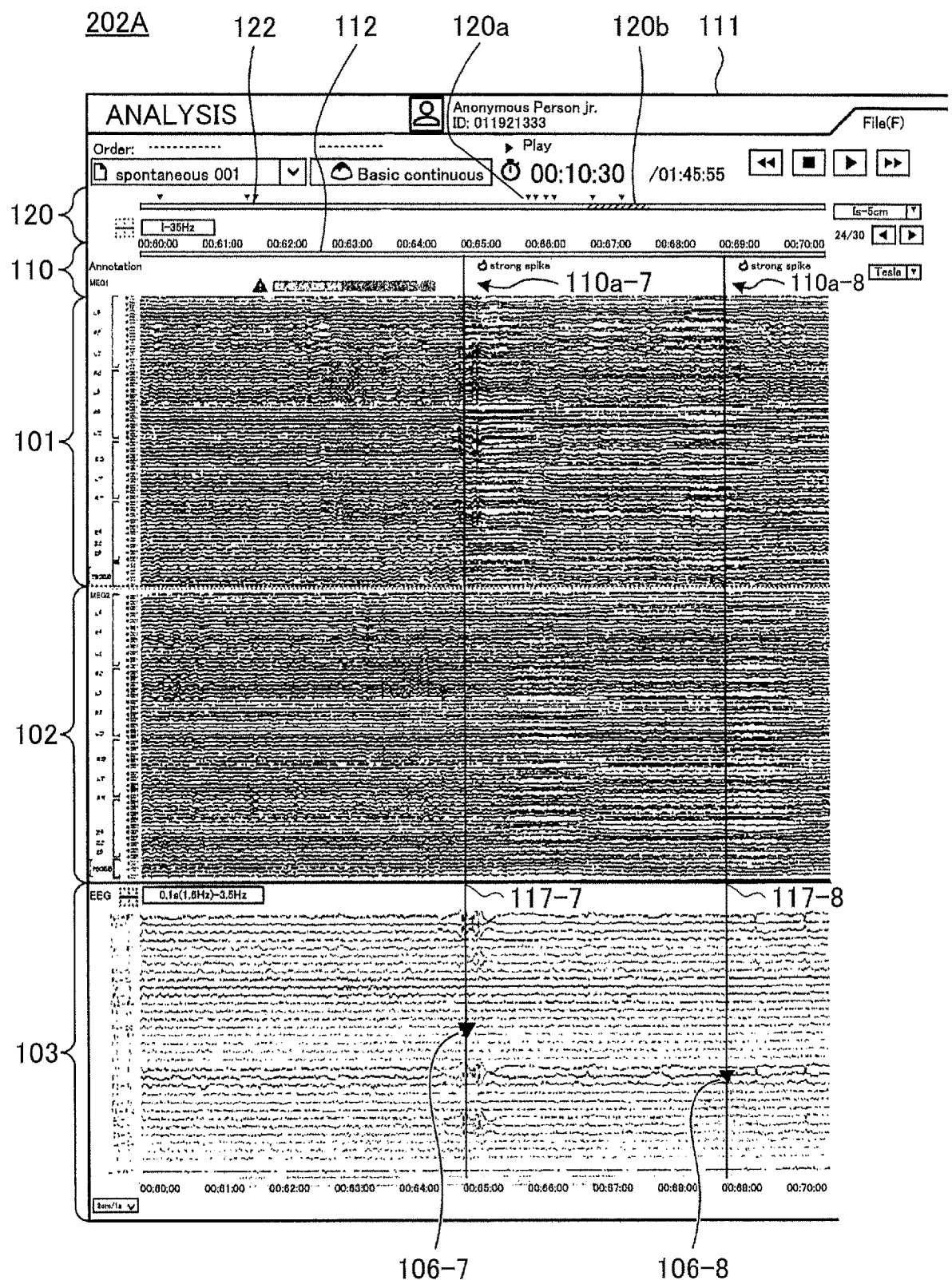
FIG. 22 is a diagram illustrating a modified example of FIG. 10.

FIG. 22 is a diagram illustrating yet another modified example of the analysis screen as illustrated in FIG. 10. In the display sections 101 through 103, annotations which were added to the signal waveforms during measurement are displayed. In the example illustrated in FIG. 22, attribute icons 106-7 and 106-8 are displayed on the location where irregular points on the waveform were designated in the display section 103. The attribute icons 106-7 and 106-8 indicate the designated location and attributes. Also, the vertical lines 117-7 and 117-8 each of which represents the time location of each attribute icon 106-7 and 106-8 are displayed in the display sections 101 through 103. The lines 117-7 and 117-8 in this example extend to the time axis 112, which can serve as functions of the annotations 110a-7 and 110a-8 respectively.

Also according to the example, an analyst can, by moving his/her eyes from the attribute icons 106-7 and 106-8 in the display section 103 to the upper region of the screen, check if there is an irregular point of the amplitude in the waveforms displayed in the display section 101 or 102 where the waveforms of the MEG signals are displayed.

Figure 23:
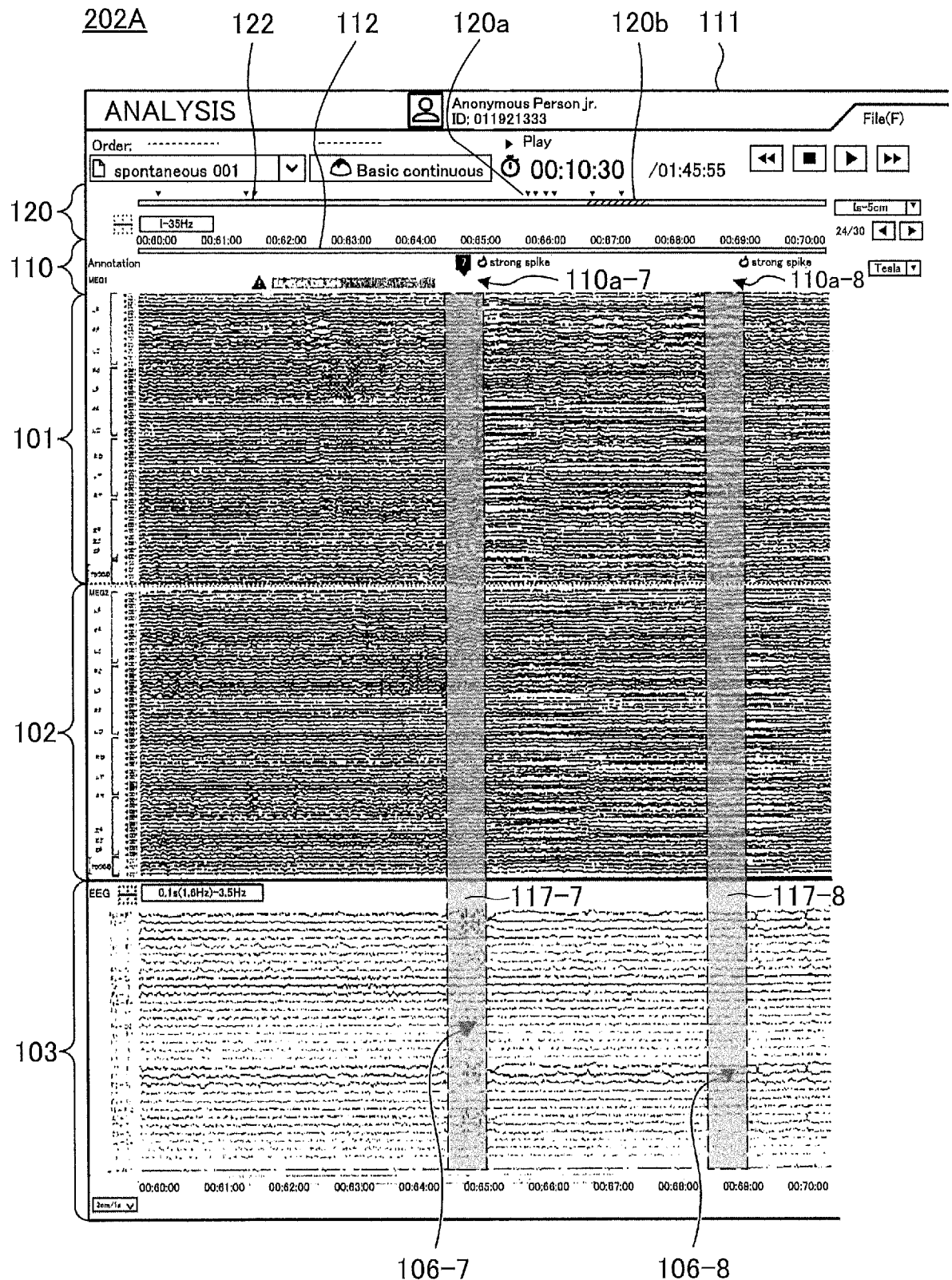
FIG. 23 is a diagram illustrating a modified example of FIG. 10.

FIG. 23 is a diagram illustrating yet another modified example of the analysis screen as illustrated in FIG. 10. In the display sections 101 through 103, annotations which were added to the signal waveforms during measurement are displayed. In the example illustrated in FIG. 23, attribute icons 106-7 and 106-8 are displayed on the location where irregular points on the waveform were designated in the display section 103. The attribute icons 106-7 and 106-8 indicate the designated location and attributes. Also, the vertical lines 117-7 and 117-8 each of which represents the time location of each attribute icon 106-7 and 106-8 are displayed in the display sections 101 through 103. The lines 117-7 and 117-8 illustrated in FIG. 23 have a certain width, and extend from the upper end of the display section 101 to the lower end of the display section 103. Attribute icons 106-7 and 106-8 are displayed so as to be respectively located in the center of each line 117-7 and 117-8.

Also according to the example, an analyst can, by moving his/her eyes from the attribute icons 106-7 and 106-8 in the display section 103 to the upper region of the screen, check if there is an irregular point of the amplitude in the waveforms displayed in the display section 101 or 102 where the waveforms of the MEG signals are displayed. Further, since the lines 117-7 and 117-8 are highlighted, or displayed with a different color from the waveforms, the visibility of the waveforms improves.

Figure 24:
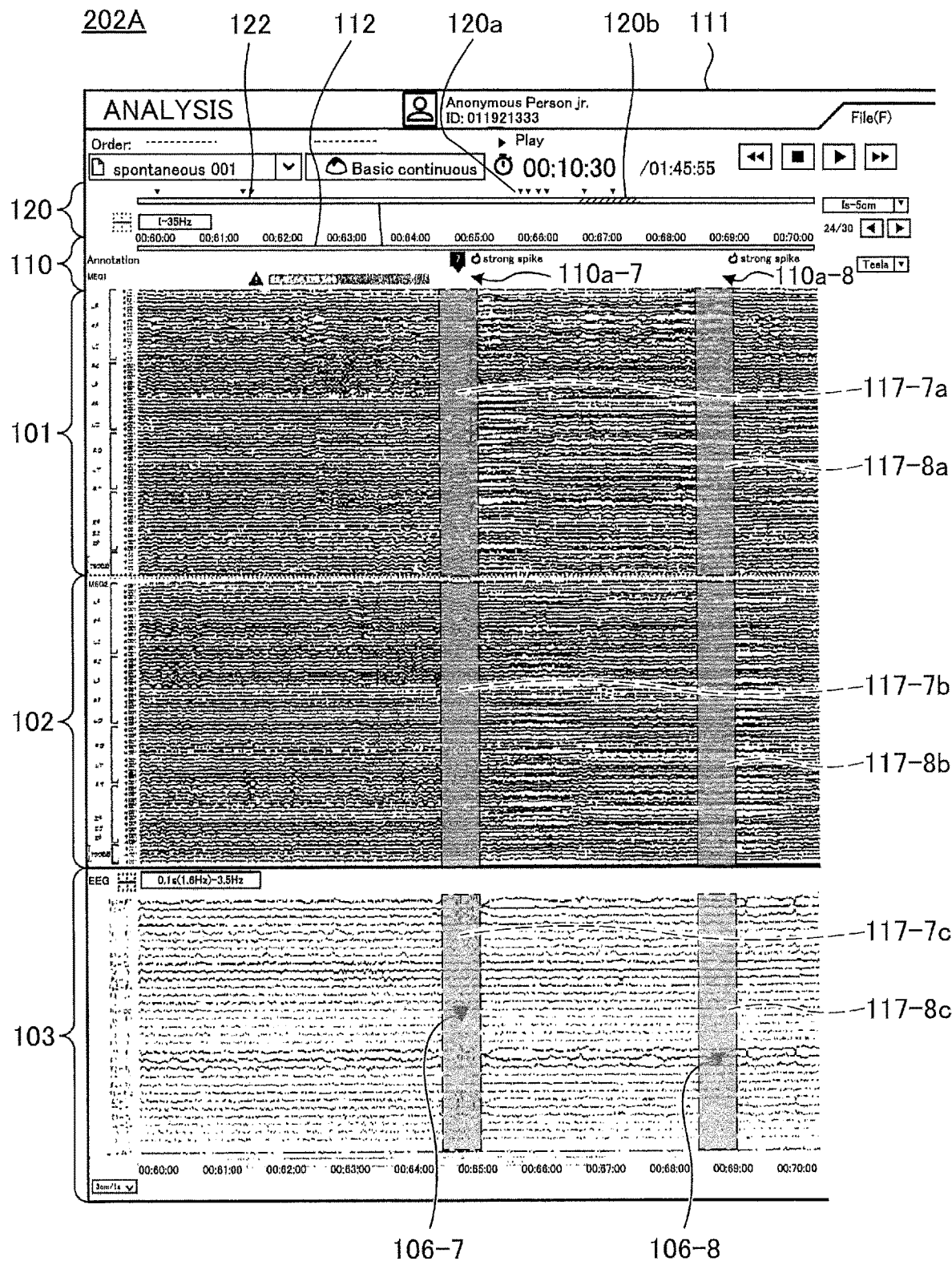
FIG. 24 is a diagram illustrating a modified example of FIG. 10.

FIG. 24 is a diagram illustrating yet another modified example of the analysis screen as illustrated in FIG. 10. FIG. 24 is different from FIG. 23 in that, while each of the lines 117-7 and 117-8 is displayed in each of the display sections 101 through 103, the lines 117-7 and 117-8 are not displayed in the area between the display sections 101 and 102, or in the area between the display sections 102 and 103.

Also according to the example, an analyst can, by moving his/her eyes from the attribute icons 106-7 and 106-8 in the display section 103 to the upper region of the screen, check if there is an irregular point of the amplitude in the waveforms displayed in the display section 101 or 102 where the waveforms of the MEG signals are displayed. Also, since the lines 117-7 and 117-8 are highlighted, or displayed with a different color from the waveforms, the visibility of the waveforms improves. Further an analyst can recognize the boundary between the display section 101 and 102, and the boundary between the display section 102 and 103 more clearly.

Figure 25:
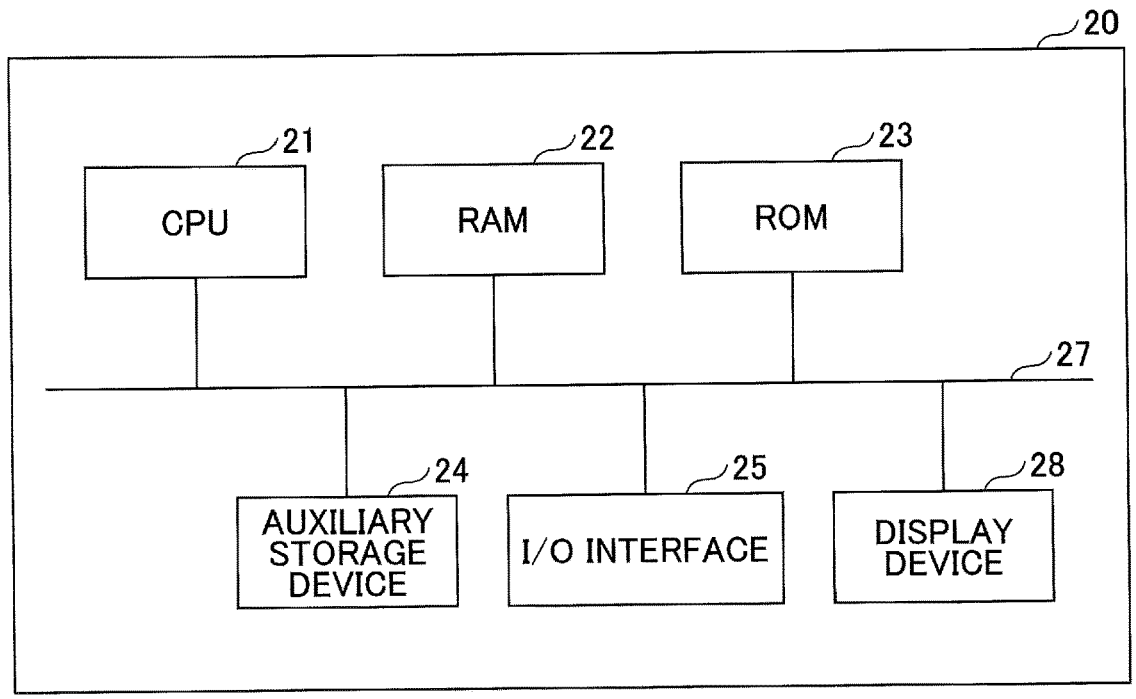
FIG. 25 is a diagram illustrating a hardware configuration of the information displaying system.

FIG. 25 is a diagram illustrating a hardware configuration of the information displaying system 20. The information displaying system 20 includes a CPU (Central Processing Unit, also referred to as "processor") 21, RAM (Random Access Memory) 22, ROM (Read Only Memory) 23, an auxiliary storage device 24, an input/output (I/O) interface 25, and a display device 28, each of which are interconnected via a bus 27.

The CPU 21 controls the overall operation of the information displaying system 20, and performs various information processing. The CPU 21 also performs display operations in the measurement screen and the analysis screen by executing an information displaying program stored in the ROM 23 or the auxiliary storage device 24. The RAM 22 is used as the work area for the CPU 21, and may include nonvolatile RAM for storing major control parameters or major information. The ROM 23 stores basic input/output (I/O) programs and the like. The information displaying program according to the present disclosure may also be stored in the ROM 23. The auxiliary storage device 24 is a storage device such as an SSD (Solid State Drive) or an HDD (Hard Disk Drive), and stores, for examples, programs for controlling the information displaying system 20, or various data or files required for operating the information displaying system 20. The input/output (I/O) interface 25 includes a user interface such as a touch panel, a keyboard, a display monitor, an operation button, and the like, and a communication interface for acquiring information from various sensors or the data recording server 42 and outputting analysis information to other electronic devices. The display device 28 corresponds to the monitor display 26. The measurement screen and the analysis screen are displayed on the display device 28, and the contents displayed on the display device 28 are updated in response to the input/output (I/O) operation via the input/output (I/O) interface 25.

Figure 26:
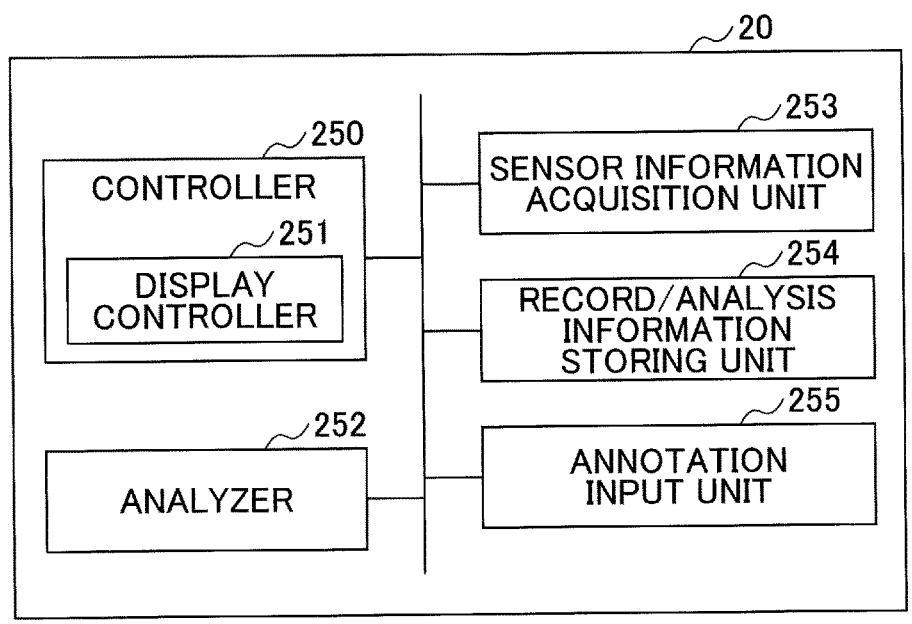
FIG. 26 is a diagram illustrating functional blocks included in the information displaying system.

FIG. 26 is a functional block diagram included in the information displaying system 20. The information displaying system 20 includes a controller 250, an analyzer 252, a sensor information acquisition unit 253, a record/analysis information storing unit 254, and an annotation input unit 255. The controller 250 includes a display controller 251 performing display operation in the information displaying system 20.

The sensor information acquisition unit 253 acquires sensor information from the measuring device 3 or the data recording server 42. The annotation input unit 255 inputs annotation information which is added to the sensor information. The analyzer 252 analyzes the acquired sensor information. The analysis of sensor information includes the analysis of signal waveforms, the analysis of an irregular point of the amplitude in the waveforms, and the analysis of brain magnetic field which includes the analysis of the direction of electrical current dipole. In the present embodiment, the analyzer 252 includes a function (function of an estimating unit) for estimating the signal source based on the signal waveforms corresponding to the annotation selected in the analysis screen. The display controller 251 performs display processing during measurement of the sensor information and during analysis by using the method described above with reference to FIGS. 2 through 24. The record/analysis information storing unit 254 stores the measured data and the analysis result. When an annotation is added to the signal waveforms during measurement, the annotation is also stored in the record/analysis information storing unit 254 by correlating with the time information at which the signal waveform was acquired. The function of the controller 250 including the display controller 251 is embodied by the CPU 21 loading a program stored in the ROM 23 and the like into the RAM 22 and executing the program. The function of the analyzer 252 is also embodied by the CPU 21 loading a program stored in the ROM 23 and the like into the RAM 22 and executing the program. Note that the function described in the present disclosure may not necessarily be embodied by the processor executing programs. For example, at least a part of the functions included in the controller 250 or the analyzer 252 may be embodied by dedicated hardware circuits (such as semiconductor integrated circuits). The function included in the sensor information acquisition unit 253 and the annotation input unit 255 is embodied by the input/output (I/O) interface 25. The function included in the record/analysis information storing unit 254 is embodied by the ROM 23 or the auxiliary storage device 24.

When the operations performed in the information displaying system 20 are embodied by executing the information displaying program, the information displaying program causes the CPU 21 (a) to display a first display section configured to display a time axis of signal detection along a first direction, (b) to display a second display section configured to display multiple signal waveforms based on the signal detection in parallel so that the signal waveforms are arranged side by side in a second direction which is different from the first direction, and (c) in response to the designation of a location on at least one of the plurality of the signal waveforms or near the at least one of the plurality of the signal waveforms in the second display section, to highlight the designated location and to display a result of the designation on a time location in the first display section corresponding to the designated location.

By installing the information displaying program described above, the information displaying system 20 can provide the display screen that facilitates recognizing the point or the region of interest of the signal waveform when multiple signal waveforms are displayed on the same time axis. The information displaying program may be provided in a state stored in a non-transitory computer-readable recording medium such as a CD-ROM, a DVD, or a USB (Universal Serial Bus) memory, and may be installed into the information displaying system 20 from the non-transitory computer-readable recording medium. Alternatively, the information displaying program may be downloaded from another computer via a network, and may be installed into the information displaying system 20.

Second Embodiment

Next, a second embodiment will be described. In the following, as for the points which are common to the above described embodiments, description will be omitted accordingly. The basic configuration of the system according to the second embodiment is the same as the system described in the first embodiment. In the embodiments described above, bio-information measured during a certain continuous period (it can be considered as a "single bio-information") is displayed on the analysis screen. But in the present embodiment, the display controller 251 is configured to treat multiple pieces of partitioned bio-information each of which includes data measured during different periods of time, and to display the signal waveforms included in one of the partitioned bio-information pieces corresponding to the timezone 120*b*.

Also, the analyzer 252 (estimation unit) performs, for each partitioned bio-information, the estimation of the signal source corresponding to an annotation selected among the annotations which were previously added to the partitioned bio-information.

<Operation of the Measurement Phase>

For example, we will assume a case that the measurement operations described in the first embodiment are executed three times intermittently. Also it is assumed that a certain interval is disposed between each measurement operation (the length of each interval may be arbitrary). Note that the number of the measurement is not limited to the case described above, that is, "three times" is just an example. The number of the measurement can be chosen appropriately depending on the purpose of the inspection.

Figure 27:
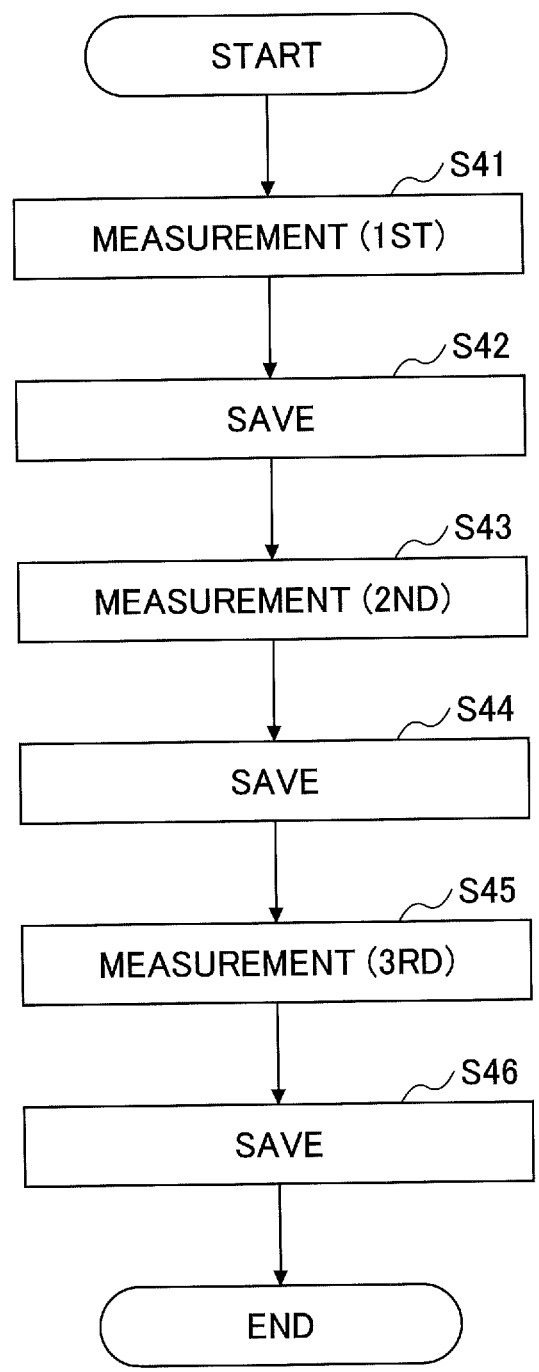
FIG. 27 is a flowchart illustrating an example of operation of the information displaying system according to a second embodiment (illustrating the operation when measurement process is performed three times)

FIG. 27 is a flowchart illustrating an example of operation performed by the information displaying system 20 according to the second embodiment (illustrating the operation when measurement process is performed three times). As illustrated in FIG. 27, the information displaying system 20 performs first measurement at step S41. The operation performed here is the same as the steps S12 through S17 illustrated in FIG. 8. After the first measurement is finished, the information displaying system 20 stores (saves) measured data including the bio-information obtained by the first measurement and the input annotation(s) into the record/analysis information storing unit 254 by correlating with a subject ID for identifying each subject (step S42).

Next, the information displaying system 20 performs second measurement (step S43). The operation performed here is the same as the steps S12 through S17 illustrated in FIG. 8. After the second measurement is finished, the information displaying system 20 stores measured data including the bio-information obtained by the second measurement and the input annotation(s) by correlating with the subject ID into the record/analysis information storing unit 254 (step S44).

Next, the information displaying system 20 performs third measurement (step S45). The operation performed here is the same as the steps S12 through S17 illustrated in FIG. 8. After the third measurement is finished, the information displaying system 20 stores measured data including the bio-information obtained by the third measurement and the input annotation(s) by correlating with the subject ID into the record/analysis information storing unit 254 (step S46).

As described above, each time a measurement (the measurement for a certain period of time) is finished, the measured data indicating the measured result is stored in the record/analysis information storing unit 254 in units of files. In the description that will be described later, a file containing measured data (the data obtained by a single measurement) stored in the record/analysis information storing unit 254 may be called "measured file". In the example described here, after the measurements were performed three times, three measured files are stored in the record/analysis information storing unit 254. In the description that will be described later, a measured file corresponding to the first measurement may be called a first measured file, a measured file corresponding to the second measurement may be called a second measured file, and a measured file corresponding to the third measurement may be called a third measured file. As described above, each measured file is stored in the record/analysis information storing unit 254 by correlating with the subject ID.

<Operation in the Analysis Phase>

Next, the operation in the analysis phase will be described. Here, it is assumed that the information displaying system 20 (display controller 251) displays a selection screen for selecting a measured file obtained by the measurement on the display device 28.

Figure 28:
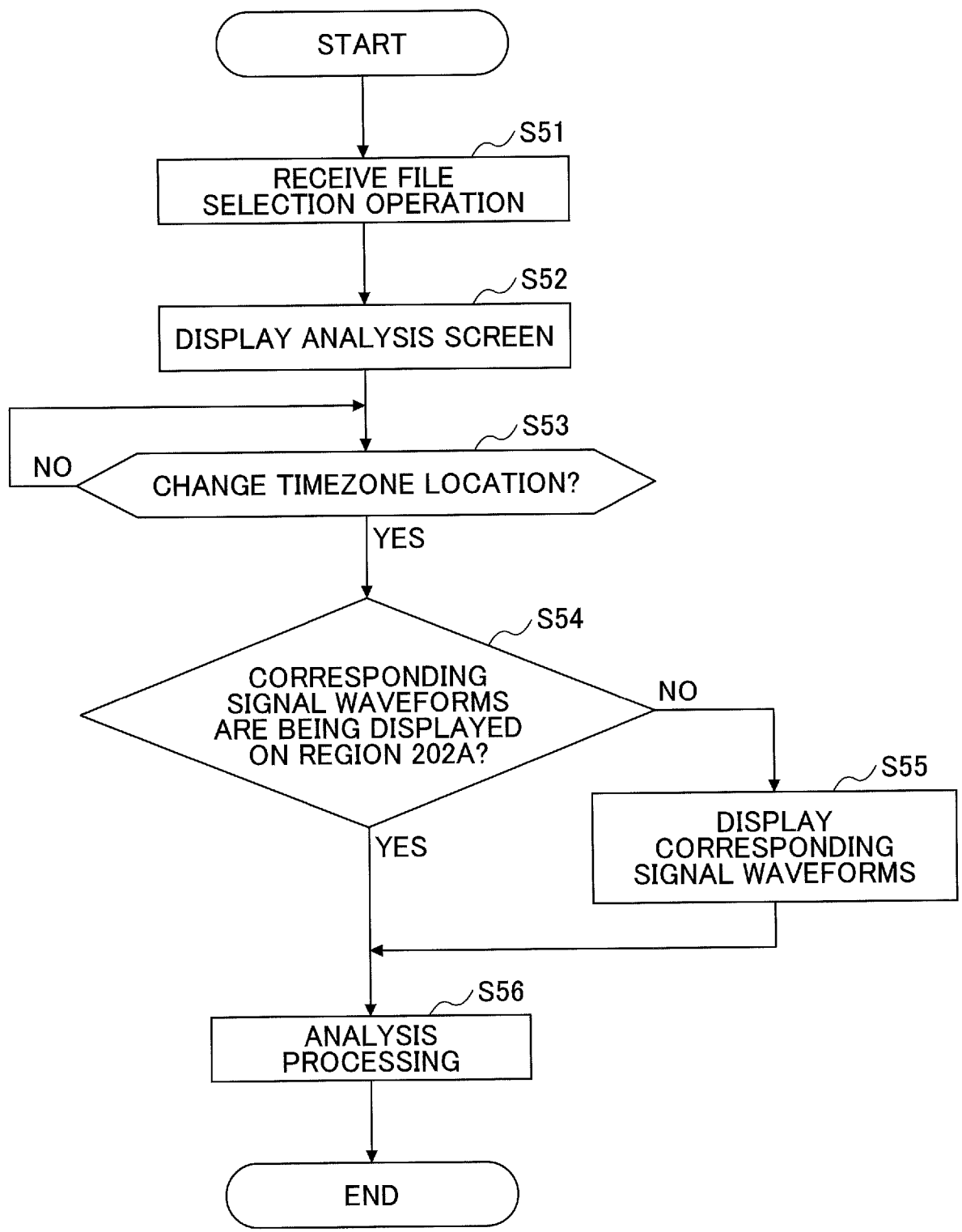
FIG. 28 is a flowchart illustrating an example of operation of the information displaying system according to the second embodiment.

FIG. 28 is a flowchart illustrating an example of operation performed by the information displaying system 20 in the analysis phase. First, the information displaying system 20 receives an operation from a user (such as an analyst) for selecting one of the measured files via the selection screen (step S51). Next, the information displaying system 20 reads a series of the measured files including the measured file selected at step S51 and other measured files with which the same subject ID as the one correlated with the selected measured file is correlated (in the example described here, the above three measured files are read), and performs the process to display, on the display device 28, an analysis screen reflecting the series of the retrieved measured files (step S52).

Figure 29:
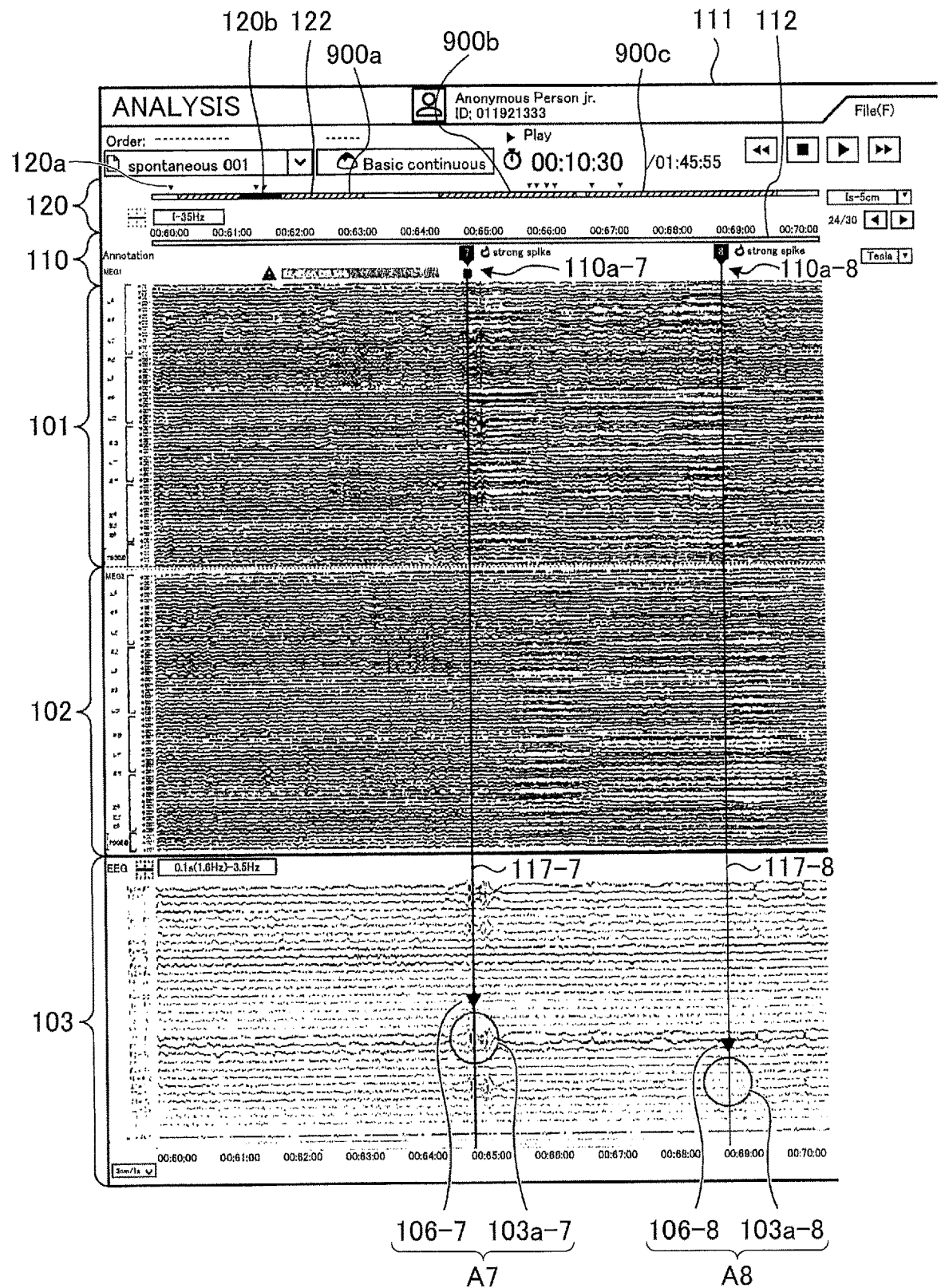
FIG. 29 is a view of the left side region of the analysis screen according to the second embodiment.

FIG. 29 is a view illustrating an example of the left side region 202A of the analysis screen that is displayed by performing the process in the step S52. The time axis 122 displays periods including the recorded times of all of the measured data stored in the series of the measured files (the first measured file, the second measured file, and the third measured file), not the recorded times of any one of the measured files. Also on the time axis 122, range information 900a representing the period when each of the measured data stored in the first measured file is recorded, range information 900b representing the period when each of the measured data stored in the second measured file is recorded, and range information 900c representing the period when each of the measured data stored in the third measured file is recorded, are displayed. Further, in each of the first measured file, second measured file, and the third measured file, pointer marks 120a indicating the time location on the signal waveforms where annotations were added are displayed along the time axis 122. In the following descriptions, the range information 900a, 900b, or 900c may simply be called "range information 900" when the range information 900a, 900b, and 900c are not distinguished from each other. The information indicating the name of the measured file may be attached to each of the range information 900. Since each measurement was performed with time intervals in the present embodiment, a gap (blank area) is disposed between each of the range information 900. An analyst can change the signal waveforms displayed on the region 202A by moving the timezone 120b using a mouse and the like. In the present embodiment, the signal waveforms corresponding to the timezone 120b (part of the bio-information contained in one of the measured files) are displayed on the region 202A. That is, an analyst can display the signal waveforms measured in the desired period of time across different measured files, by moving the timezone 120b on the time axis 122.

In the present embodiment, all annotations included in each of the three measured files are displayed on the annotation list 180 that resides in the region 202B in the right side of the analysis screen. Further, for example, the information displaying system 20 may also be configured to manage each measured file by correlating with a name of the inspection and to display the name of the inspection correlated with the measured file corresponding to the timezone 120b on the analysis screen.

Referring to the description of FIG. 28, if the information displaying system 20 received an operation from an analyst to change the location of the timezone 120b (YES at step S53) after displaying the analysis screen at S52, the information displaying system 20 determines whether the signal waveforms corresponding to the current location of the timezone 120b are being displayed on the region 202A or not (step S54).

If the result of the determination at step S54 is negative (NO at step S54), the information displaying system 20 displays the signal waveforms corresponding to the current location of the timezone 120b on the region 202A (step S55). If the result of the determination at step S54 is positive (YES at step S54) or after executing step S55, the information displaying system 20 performs analysis processing in accordance with the operation from an analyst (step S56). The analysis processing performed here is the steps S23 through S31 illustrated in FIG. 15.

First Modified Example of the Second Embodiment

Figure 30:
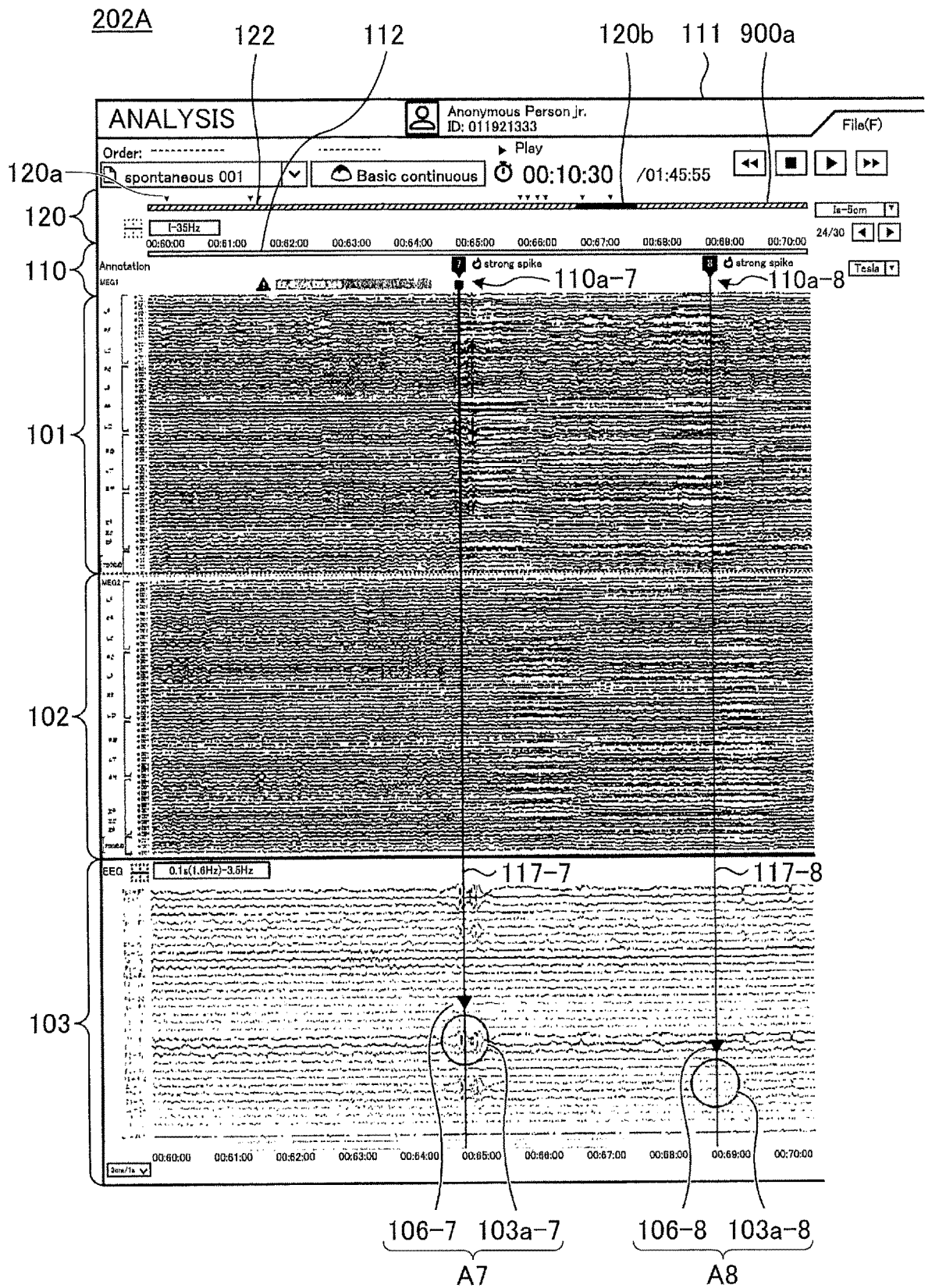
FIG. 30 is a view illustrating an example of the analysis screen according to a modified example of the second embodiment.

FIG. 30 is a view illustrating an example of the analysis screen according to a first modified example of the second embodiment. In the first modified example of the second embodiment, for example, only a single range information 900 corresponding to one of the measured files is displayed on the time axis 122 in the analysis screen, and the range information 900 to be displayed on the time axis 122 may be changed in units of measured files, in response to the operation of an analyst. In the example illustrated in FIG. 30, only the range information 900*a* is displayed, which represents the period when each of the measured data stored in the first measured file is recorded. When the information displaying system receives an operation from an analyst to change the range information 900, the information displaying system 20 changes the range information 900 to be displayed on the time axis 122 in units of measured files in response to the operation. Also, in accordance with the change of the range information, the information displaying system 20 changes the contents to be displayed in the region 202A and 202B so that the contents related to the measured file corresponding to the changed range information 900 can be displayed.

Second Modified Example of the Second Embodiment

In the second embodiment, the information displaying system 20 is configured such that the timezone 120*b* is not placed across the multiple range information. For example, we will assume the case that the information displaying system 20 receives the instruction to advance the timezone 120*b* slightly when the timezone 120*b* is located at the tail of the range information 900*a* illustrated in FIG. 29. In this case, the information displaying system 20 changes the location of the timezone 120*b* so that the timezone 120*b* is not placed between the range information 900*a* and 900*b* but located at the head of the range information 900*b*.

Figure 31A:
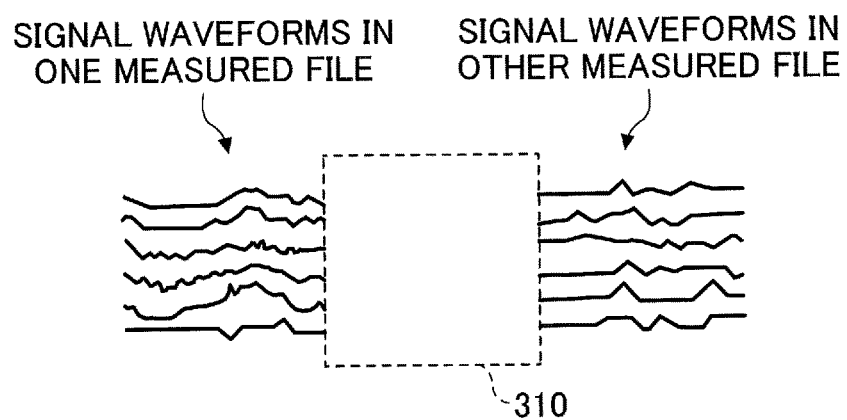
FIG. 31A is a view for explaining a displaying method for distinctively illustrating the signal waveforms each of which is based on the different range information.
Figure 31B:
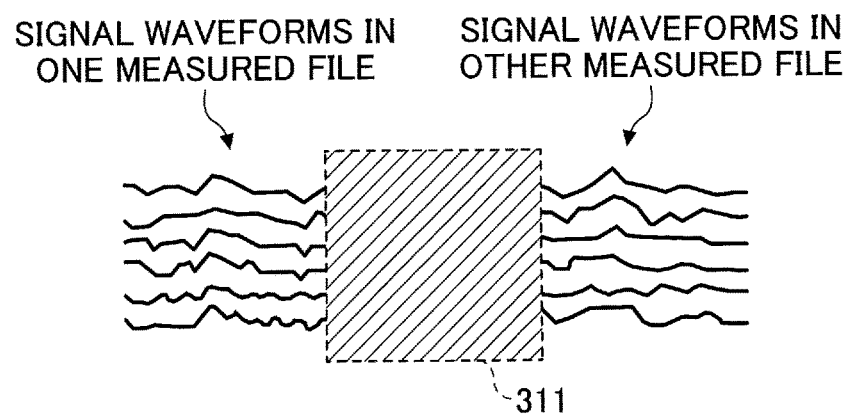
FIG. 31B is a view for explaining a displaying method for distinctively illustrating the signal waveforms each of which is based on the different time range information.

However, the way of the placement of the timezone 120*b* is not limited to the example described above. In the second modified example of the second embodiment, the information displaying system 20 allows the timezone 120*b* to be placed over multiple range information 900. In this case, as illustrated in FIG. 31A, the signal waveforms corresponding to the timezone 120*b* displayed in the display sections 101 through 103 contains the blank area 310 (corresponding to the interval between measurements) where no bio-information exists. For example, the information displaying system 20 may be configured to display the waveforms with changing the background of the blank area 311 in order to make an analyst recognize that the area 311 represents an area between different measured files, as illustrated in FIG. 31B.

Figure 32A:
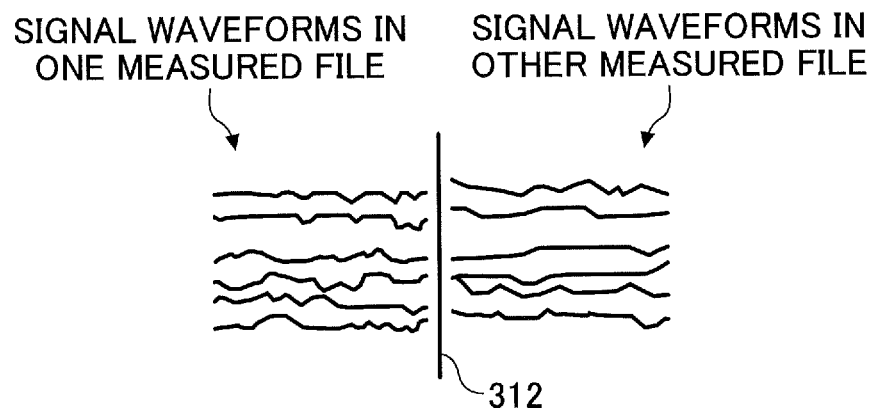
FIG. 32A is a view for explaining a displaying method for distinctively illustrating the signal waveforms each of which is based on the different time range information.
Figure 32B:
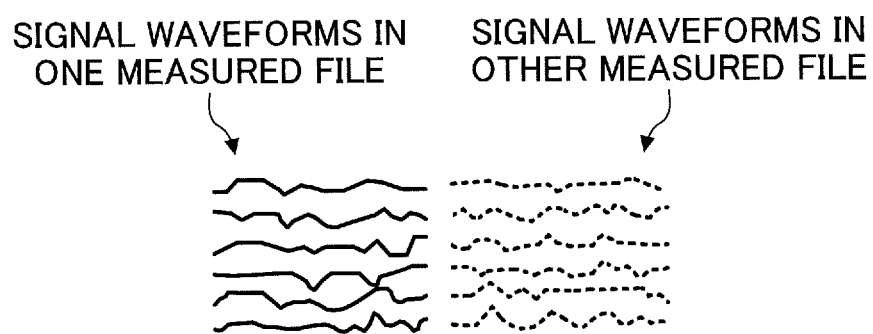
FIG. 32B is a view for explaining a displaying method for distinctively illustrating the signal waveforms each of which is based on the different time range information.
Figure 32C:
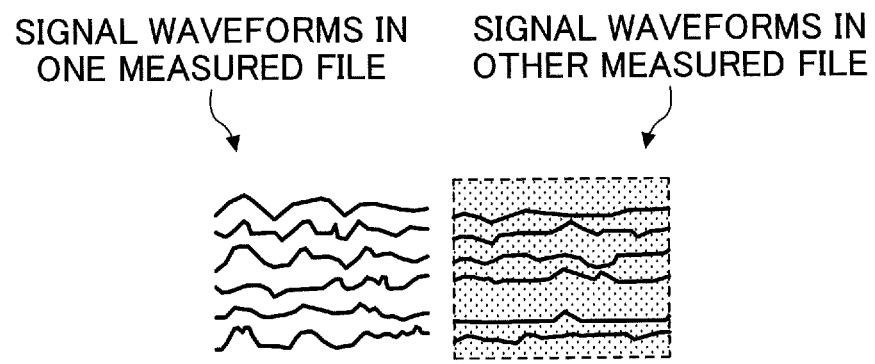
FIG. 32C is a view for explaining a displaying method for distinctively illustrating the signal waveforms each of which is based on the different range information.

Further, when the timezone 120*b* is placed over the multiple range information 900 and the interval between each measurement is short, little gap may exist between the signal waveforms corresponding to one measured file and the signal waveforms corresponding to the other measured file. In this case, as illustrated in FIG. 32A, the information displaying system 20 may be configured to display the line 312 (which is different from an annotation line) representing a junction between the signal waveforms corresponding to one measured file and the signal waveforms corresponding to the other measured file. Also, for example, as illustrated in FIG. 32B, the information displaying system 20 may be configured to display the signal waveforms corresponding to one measured file in a different style from the signal waveforms corresponding to the other measured file. Or, as illustrated in FIG. 32C, the information displaying system 20 may be configured to display the background of the signal waveforms corresponding to one measured file in a different color from the color of the background of the signal waveforms corresponding to the other measured file.

In the embodiments described above, the measuring device 3 is configured to collect EEG signals and MEG signals, but other configurations may be adopted. For example, the biosignal measurement system 1 may be configured to collect MEG signals using the measuring device 3, to collect EEG signals using an electroencephalograph other than the measuring device 3, and to send each biosignal obtained from the measuring device 3 and the electroencephalograph to the data recording server 42.

The information displaying technique described in the present disclosure can be applied not only to the case for displaying EEG signals and MEG signals side by side, but also to the case for displaying a large number of electrocardiograms and nervous signals on the same time axis using a electrocardiograph or a spinal cord meter. Also the technique can be applied to a geological exploration system for analyzing a magnetic field using a large number of geomagnetic sensors to display the signal waveforms on the same time axis. Alternatively, the technique can be applied to sites performing quality control to display signal waveforms on the same time axis collected from a large number of sensors such as convection current meters (heat flow sensors), dew condensation meters (humidity sensors), and the like.

Although the present invention has been described with reference to embodiments, the present invention is not limited to these embodiments, but various variations and modifications may be made without departing from the scope of the invention as set forth in the accompanying claims.

What is claimed is:

1. An information displaying system comprising:
   a memory storing a program;
   a display device, and
   a processor configured to execute the program to implement a process including:
   displaying a time axis region on the display device, the time axis region being configured to display a first time axis of a biosignal along a first direction, to display a second time axis of the biosignal along the first direction, and to display a first mark on the first time axis in the time axis region, the first time axis representing an entire period of time when the biosignal was measured, and the first mark being a pointer mark indicating a time point designated by a user,
   displaying a signal display region on the display device, the signal display region being configured to display a plurality of waveforms of the biosignal side by side in a second direction which is different from the first direction, the second time axis displayed on the time axis region representing a period of time when the waveforms displayed on the signal display region were obtained;
   in response to receiving, from the user, an operation of designating a specific time point on the signal display region, displaying the first mark at a location on the first time axis in the time axis region corresponding to the specific time point on the signal display region; and
   in response to receiving an operation of designating a section on the first time axis in the time axis region from the user,
   displaying, in the signal display region, the plurality of waveforms for a time range corresponding to the designated section on the first time axis, and in a case in which the first mark displayed on the first time axis is located within the designated section on the first time axis, displaying, in the signal display region, a line crossing the plurality of waveforms in the second direction at the time point indicated by the first mark.

2. The information displaying system according to claim 1, wherein the time axis region is configured to display a plurality of the first marks.

3. The information displaying system according to claim 2, the process further including
displaying a counter box on the display device configured to display a number of the first marks.

4. The information displaying system according to claim 2, wherein the signal display region is configured to display a plurality of lines each corresponding to one of the plurality of the first marks.

5. The information displaying system according to claim 1, wherein the time axis region is configured, to display figures of time, in addition to the first time axis and the second time axis.

6. The information displaying system according to claim 1, wherein the biosignal is a magnetoencephalogram (MEG) signal.

7. The information displaying system according to claim 1, wherein the biosignal includes a magnetoencephalogram (MEG) signal and an electroencephalogram (EEG) signal, and the waveforms of the MEG signal and the waveforms of the EEG signal are displayed on the signal display region in a synchronized manner.

8. The information displaying system according to claim 1, wherein information of the biosignal and the first mark is stored in the memory as a measured file, and the plurality of waveforms are displayed by reading out the measured file from the memory.

9. The information displaying system according to claim 1, wherein, in displaying the line, a second mark corresponding to the line is displayed between the time axis region and the signal display region, and the line is displayed such that an end of the line is in contact with the second mark.

10. An information displaying device comprising:
a memory storing a program;
a display device; and
a processor configured to execute the program to implement a process including:
displaying a time axis region on the display device, the time axis region being configured to display a first time axis of a biosignal along a first direction to display a second time axis of the biosignal along the first direction, and to display a first mark on the first time axis in the time axis region, the first time axis representing an entire period of time when the biosignal was measured, and the first mark being a pointer mark indicating a time point designated by a user;
displaying a signal display region on the display device, the signal display region being configured to display a plurality of waveforms of the biosignal side by side in a second direction which is different from the first direction, the second time axis displayed on the time axis region representing a period of time when the waveforms displayed on the signal display region were obtained;
in response to receiving, from the user, an operation of designating a specific time point on the signal display region, displaying the first mark at a location on the first time axis in the time axis region corresponding to the specific time point on the signal display region; and
in response to receiving an operation of designating a section on the first time axis in the time axis region from the user,
displaying, in the signal display region, the plurality of waveforms for a time range corresponding to the designated section on the first time axis, and
in a case in which the first mark displayed on the first time axis is located within the designated section on the first time axis, displaying, in the signal display region, a line crossing the plurality of waveforms in the second direction at the time point indicated by the first mark.

11. A non-transitory computer-readable recording medium storing a computer program to cause a processor in an information displaying device including a display device to execute a method, the method comprising:
displaying a time axis region on the display device, the time axis region being configured to display a first time axis of a biosignal along a first direction, to display a second time axis of the biosignal along the first direction, and to display a first mark on the time axis in the time axis region, the first time axis representing an entire period of time when the biosignal was measured, and the first mark being a pointer mark indicating a time point designated by a user;
displaying a signal display region on the display device, the signal display region being configured to display a plurality of waveforms of the biosignal side by side in a second direction which is different from the first direction, the second time axis displayed on the time axis region representing a period of time when the waveforms displayed on the signal display region were obtained;
in response to receiving, from the user, an operation of designating a specific time point on the signal display region, displaying the first mark at a location on the first time axis in the time axis region corresponding to the specific time point on the signal display region, and
in response to receiving an operation of designating a section on the first time axis in the time axis region from the user,
displaying, in the signal display region, the plurality of waveforms for a time range corresponding to the designated section on the first time axis, and
in a case in which the first mark displayed on the first time axis is located within the designated section on the first time axis, displaying, in the signal display region, a line crossing the plurality of waveforms in the second direction at the time point indicated by the first mark.

* * * * *